United States Patent
Alnemri et al.

(12) 
(10) Patent No.: US 6,287,795 B1
(45) Date of Patent: Sep. 11, 2001

(54) MCH4 AND MCH5, APOPTOTIC PROTEASE, NUCLEIC ACIDS ENCODING AND METHODS OF USE

(75) Inventors: Emad S. Alnemri; Teresa Fernandes-Alnemri, both of Ambler; Gerald Litwack, Wynnewood, all of PA (US); Robert Armstrong, San Diego; Kevin Tomaselli, La Jolla, both of CA (US)

(73) Assignees: Thomas Jefferson University, Philadelphia, PA (US); IDUN Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/291,692

(22) Filed: Apr. 13, 1999

Related U.S. Application Data

(63) Continuation of application No. 08/882,429, filed on Jun. 25, 1997, now abandoned, which is a continuation of application No. 08/665,220, filed on Jun. 14, 1996, now Pat. No. 5,786,173, which is a continuation of application No. 08/618,408, filed on Mar. 19, 1996, now Pat. No. 5,851,815.

(51) Int. Cl.$^7$ ..................................................... C12Q 1/37
(52) U.S. Cl. ........................ 435/23; 435/7.21; 435/7.91; 435/7.72; 435/325; 435/219; 536/23.2
(58) Field of Search .................................. 435/325, 219, 435/6; 536/23.2

(56) References Cited

PUBLICATIONS

Fernandes–Alnemri et al., Mch3, A Novel Human Apoptotic Cysteine Protease Highly Related to CPP32, *Cancer Research* 55(24):6045–6052 (1995).
Gagliardini et al., "Prevention of Vertebrate Neuronal Death by the crmA Gene", *Science* 263:826–828 (1994).
Hillier et al., "The WashU–Merck EST Project", EMBL/Genbank Databases, Accession No. T96912, Sequence Reference HS91272 (1995).
Hillier et al., "The WashU–Merck EST Project", EMBL/Genbank Databases, Accession No. N42544, Sequence Reference HS544281 (1996).
Howard et al., "IL–1–Converting Enzyme Requires Aspartic Acid Residues for Processing of the IL–1–β Precursor at Two Distinct Sites and Does Not Cleave 31–kDa IL–1α", *J. Immunol.* 147:2964–2969 (1991).
Hsu et al., "TRADD–TRAF2 and TRADD–FADD Interactions Define Two Distinct THF Receptor 1 Signal Transduction Pathways," *Cell* 84:299–308 (1996).
Kischkel et al., "Cytotoxicity–dependent APO–1 (Fas/CD95)–associated proteins form a death–inducing signaling complex (DISC) with the receptor", *The EMBO Journal* 14(22):5579–5588 (1995).
Korsmeyer, Stanley J., "Regulators of cell death", *TIG* 11(3):101–105 (1995).

Kostura et al., "Identification of a monocyte specific pre–interleukin 1β convertase activity", *Proc. Natl. Acad. Sci. USA* 86:5227–5231 (1989).
Kumar et al., "Induction of apoptosis by the mouse Nedd2 gene, which encodes a protein similar to the product of the *Caenorhabditis elegans* cell death gene ced–3 and the mammalian IL–1β–converting enzyme," *Genes Dev.* 8:1613–1626 (1994).
Los et al., "Requirement of an ICE/CED–3 protease for Fas/APO–1–mediated apoptosis", *Nature* 375:81–83 (1995).
Mann, M. and Wilm, M., "Electrospray mass spectrometry for protein characterization", *TIBS Trends in Biochemical Sciences* 20:219–224 (1995).
Miura et al., "Induction of Apoptosis in Fibroblasts by IL–1β–Converting Enzyme, a Mammalian Homolog of the *C. elegans* Cell Death Gene ced–3", *Cell* 75:653–660 (1993).
Nagata and Golstein, "The Fas Death Factor", *Science* 267:1449–1456 (1995).
Wang et al., "Ich–1, and Ice/ced–3–Related Gene, Encodes Both Positive and Negative Regulators of Programmed Cell Death", *Cell* 78:739–750 (1994).
Williams, Gwyn T., and Smith, Christopher A., "Molecular Regulation of Apoptosis: Genetic Controls on Cell Death", *Cell* 74:777–779 (1993).
Wilm et al., "Femtomole sequencing of proteins from polyacrylamide gels by nano–electrospray mass spectrometry", *Nature* 379:466–469 (1996).
Wilson et al., "Structure and Mechanism of Interleukin–1β Converting Enzyme", *Nature* 370:270–275 (1994).
Yuan et al., "The *C. elegans* Cell Death Gene ced–3 Encodes a Protein Similar to Mammalian Interleukin–1β–Converting Enzyme", *Cell* 75:641–652 (1993).
Ray et al., "Viral Inhibition of Inflammation: Cowpox Virus Encodes an Inhibitor of the Interleukin–1β Converting Enzyme", *Cell* 69:597–604 (1992).

(List continued on next page.)

*Primary Examiner*—Karen Cochrane Carlson
*Assistant Examiner*—Patricia Robinson
(74) *Attorney, Agent, or Firm*—Seed Intellectual Property Law Group PLLC

(57) ABSTRACT

The invention provides an isolated gene encoding Mch4 or an isolated gene encoding Mch5 as well as functional fragments thereof. Also provided are isolated nucleic acid sequences encoding Mch4 or Mch5 or functional fragment thereof The gene or nucleic acid sequences can be single or double stranded nucleic acids corresponding to coding or non-coding strands of the Mch4 or Mch5 nucleotide sequences. Also provided are genes and nucleic acids encoding functional fragments such as the FADD-like domains Mch4A, Mch4B, Mch5A and Mch5B. Isolated Mch4 or Mch5 polypeptides or functional fragments thereof including the FADD-like domains Mch4A, Mch4B, Mch5A and Mch5B are also provided.

10 Claims, 13 Drawing Sheets

OTHER PUBLICATIONS

Reed, John C., "Mini–Review: Cellular Mechanisms of Disease Series: Bcl–2 and the Regulation of Programmed Cell Death", *J. Cell Biol.* 124:1–6 (1994).

Sleath et al., "Substrate Specificity of the Protease That Processes Human Interleukin–1β", *J. Biol. Chem.* 265:14526–14528 (1990).

Steller, Hermann, "Mechanisms and Genes of Cellular Suicide", *Science* 267:1445–1449 (1995).

Thompson, Craig B., "Apoptosis in the Pathogenesis and Treatment of Disease", *Science* 267:1456–1462 (1995).

Thornberry et al., "A novel heterodimeric cysteine protease is required for interleukin–1β processing in monocytes", *Nature* 356:768–774 (1992).

Walker et al., "Crystal Structure of the Cysteine Protease Interleukin–1β–Converting Enzyme: A $(p20/p10)_2$ Homodimer", *Cell* 78:343–352 (1994).

```
TGAAGTCTCTTCCCAAGCAAATGGGAGCTTCTTTGGACCTTGGAGCACACAGAGGATTCTACTTTCTTTAAAACTTTGTT  80

TTCAGGCAATTTCCCTGAGAACCGTTTACTTCCAGAAGATTGGTGGAGCTTGATCTGAAGGCTGGCCATGAAATCTCAAG 160
                                                                  M  K  S  Q

GTCAACATTGGTATTCCAGTTCAGATAAAAACTGTAAAGTGAGCTTTCGTGAGAAGCTTCTGATTATTGATTCAAACCTG 240
 G  Q  H  W  Y  S  S  S  D  K  N  C  K  V  S  F  R  E  K  L  L  I  I  D  S  N  L

GGGGTCCAAGATGTGGAGAACCTCAAGTTTCTCTGCATAGGATTGGTCCCCAACAAGAAGCTGGAGAAGTCCAGCTCAGC 320
 G  V  Q  D  V  E  N  L  K  F  L  C  I  G  L  V  P  N  K  K  L  E  K  S  S  S  A

CTCAGATGTTTTTGAACATCTCTTGGCAGAGGATCTGCTGAGTGAGGAAGACCCTTTCTTCCTGGCAGAACTCCTCTATA 400
  S  D  V  F  E  H  L  L  A  E  D  L  L  S  E  E  D  P  F  F  L  A  E  L  L  Y

TCATACGGCAGAAGAAGCTGCTGCAGCACCTCAACTGTACCAAAGAGGAAGTGGAGCGACTGCTGCCCACCCGACAAAGG 480
 I  I  R  Q  K  K  L  L  Q  H  L  N  C  T  K  E  E  V  E  R  L  L  P  T  R  Q  R

GTTTCTCTGTTTAGAAACCTGCTCTACGAACTGTCAGAAGGCATTGACTCAGAGAACTTAAAGGACATGATCTTCCTTCT 560
  V  S  L  F  R  N  L  L  Y  E  L  S  E  G  I  D  S  E  N  L  K  D  M  I  F  L  L

GAAAGACTCGCTTCCCAAAACTGAAATGACCTCCCTAAGTTTCCTGGCATTTCTAGAGAAACAAGGTAAAATAGATGAAG 640
   K  D  S  L  P  K  T  E  M  T  S  L  S  F  L  A  F  L  E  K  Q  G  K  I  D  E

ATAATCTGACATGCCTGGAGGACCTCTGCAAAACAGTTGTACCTAAACTTTTGAGAAACATAGAGAAATACAAAAGAGAG 720
 D  N  L  T  C  L  E  D  L  C  K  T  V  V  P  K  L  L  R  N  I  E  K  Y  K  R  E

AAAGCTATCCAGATAGTGACACCTCCTGTAGACAAGGAAGCCGAGTCGTATCAAGGAGAGGAAGAACTAGTTTCCCAAAC 800
  K  A  I  Q  I  V  T  P  P  V  D  K  E  A  E  S  Y  Q  G  E  E  E  L  V  S  Q  T
```

*Fig. 1A*

```
AGATGTTAAGACATTCTTGGAAGCCTTACCGAGGGCAGCTGTGTACAGGATGAATCGGAACCACAGAGGCCTCTGTGTCA 880

D  V  K  T  F  L  E  A  L  P  R  A  A  V  Y  R  M  N  R  N  H  R  G  L  C  V

TTGTCAACAACCACAGCTTTACCTCCCTGAAGGACAGACAAGGAACCCATAAAGATGCTGAGATCCTGAGTCATGTGTTC 960

I  V  N  N  H  S  F  T  S  L  K  D  R  Q  G  T  H  K  D  A  E  I  L  S  H  V  F

CAGTGGCTTGGGTTCACAGTGCATATACACAATAATGTGACGAAAGTGGAAATGGAGATGGTCCTGCAGAAGCAGAAGTG 1040

Q  W  L  G  F  T  V  H  I  H  N  N  V  T  K  V  E  M  E  M  V  L  Q  K  Q  K  C

CAATCCAGCCCATGCCGACGGGGACTGCTTCGTGTTCTGTATTCTGACCCATGGGAGATTTGGAGCTGTCTACTCTTCGG 1120

N  P  A  H  A  D  G  D  C  F  V  F  C  I  L  T  H  G  R  F  G  A  V  Y  S  S

ATGAGGCCCTCATTCCCATTCGGGAGATCATGTCTCACTTCACAGCCCTGCAGTGCCCTAGACTGGCTGAAAAACCTAAA 1200

D  E  A  L  I  P  I  R  E  I  M  S  H  F  T  A  L  Q  C  P  R  L  A  E  K  P  K

CTCTTTTTCATCCAGGCCTGCCAAGGTGAAGAGATACAGCCTTCCGTATCCATCGAAGCAGATGCTCTGAACCCTGAGCA 1280

L  F  F  I  Q  A  C  Q  G  E  E  I  Q  P  S  V  S  I  E  A  D  A  L  N  P  E  Q

GGCACCCACTTCCCTGCAGGACAGTATTCCTGCCGAGGCTGACTTCCTACTTGGTCTGGCCACTGTCCCAGGCTATGTAT 1360

A  P  T  S  L  Q  D  S  I  P  A  E  A  D  F  L  L  G  L  A  T  V  P  G  Y  V

CCTTTCGGCATGTGGAGGAAGGCAGCTGGTATATTCAGTCTCTGTGTAATCATCTGAAGAAATTGGTCCCAAGACATGAA 1440

S  F  R  H  V  E  E  G  S  W  Y  I  Q  S  L  C  N  H  L  K  K  L  V  P  R  H  E

GACATCTTATCCATCCTCACTGCTGTCAACGATGATGTGAGTCGAAGAGTGGACAAACAGGGAACAAAGAAACAGATGCC 1520

D  I  L  S  I  L  T  A  V  N  D  D  V  S  R  R  V  D  K  Q  G  T  K  K  Q  M  P

CCAGCCTGCTTTCACACTAAGGAAAAAACTAGTATTCCCTGTGCCCCTGGATGCACTTTCAATATAGCAGAGAGTTTTTG 1600

Q  P  A  F  T  L  R  K  K  L  V  F  P  V  P  L  D  A  L  S  I

NTGGTTCTTAGACCTCAAACGAATCATTGGGNTATAACCTCCAGCCTCCTGCCCAGCACAGGAATCGGTGGTCTCCACCTG 1680

TCATTCTAGAAACAGGAAAC 1700
```

*Fig. 1B*

```
TGAAGGCTGGTTGTTCAGACTGAGCTTTCCTGCCTGCCTGTACCCCGCCAACAGCTTCAGAAGAAGGTGACTGGTGGCTGC  80

CTGAGGAATACCAGTGGGCAAGAGAATTAGCATTTCTGGAGCATCTGCTGTCTGAGCAGCCCCTGGGTGCGTCCACTTTC  160

TGGGCACGTGAGGTTGGGCCTTGGCCGCCTGAGCCCTTGAGTTGGTCACTTGAACCTTGGGAAATATTGAGATTATATTCT  240

CCTGCCTTTTAAAAAGATGGACTTCAGCAGAAATCTTTATGATATTGGGGAACAACTGGACAGTGAAGATCTGGCCTCCC  320
                 M  D  F  S  R  N  L  Y  D  I  G  E  Q  L  D  S  E  D  L  A  S

TCAAGTTCCTGAGCCTGGACTACATTCCGCAAAGGAAGCAAGAACCCATCAAGGATGCCTTGATGTTATTCCAGAGACTC  400
 L  K  F  L  S  L  D  Y  I  P  Q  R  K  Q  E  P  I  K  D  A  L  M  L  F  Q  R  L

CAGGAAAAGAGAATGTTGGAGGAAAGCAATCTGTCCTTCCTGAAGGAGCTGCTCTTCCGAATTAATAGACTGGATTTGCT  480
   Q  E  K  R  M  L  E  E  S  N  L  S  F  L  K  E  L  L  F  R  I  N  R  L  D  L

GATTACCTACCTAAACACTAGAAAGGAGGAGATGGAAAGGGAACTTCAGACACCAGGCAGGGCTCAAATTTCTGCCTACA  560
 L  I  T  Y  L  N  T  R  K  E  E  M  E  R  E  L  Q  T  P  G  R  A  Q  I  S  A  Y

GGTTCCACTTCTGCCGCATGAGCTGGGCTGAAGCAAACAGCCAGTGCCAGACACAGTCTGTACCTTTCTGGCGGAGGGTC  640
   R  F  H  F  C  R  M  S  W  A  E  A  N  S  Q  C  Q  T  Q  S  V  P  F  W  R  R  V

GATCATCTATTAATAAGGGTCATGCTCTATCAGATTTCAGAAGAAGTGAGCAGATCAGAATTGAGGTCTTTTAAGTTTCT  720
 D  H  L  L  I  R  V  M  L  Y  Q  I  S  E  E  V  S  R  S  E  L  R  S  F  K  F  L

TTTGCAAGAGGAAATCTCCAAATGCAAACTGGATGATGACATGAACCTGCTGGATATTTTCATAGAGATGGAGAAGAGGG  800
   L  Q  E  E  I  S  K  C  K  L  D  D  D  M  N  L  L  D  I  F  I  E  M  E  K  R

TCATCCTGGGAGAAGGAAAGTTGGACATCCTGAAAAGAGTCTGTGCCCAAATCAACAAGAGCCTGCTGAAGATAATCAAC  880
 V  I  L  G  E  G  K  L  D  I  L  K  R  V  C  A  Q  I  N  K  S  L  L  K  I  I  N

GACTATGAAGAATTCAGCAAAGGGGAGGAGTTGTGTGGGGTAATGACGATGTCGGACTGTCCAAGAGAACAGGATAGTGA  960
   D  Y  E  E  F  S  K  G  E  E  L  C  G  V  M  T  M  S  D  C  P  R  E  Q  D  S  E
```

*Fig. 2A*

```
ATCACAGACTTTGGACAAAGTTTACCAAATGAAAAGCAAGCCTCGGGGATACTGTCTGATCATCAACAATCACAATTTTG 1040

S  Q  T  L  D  K  V  Y  Q  M  K  S  K  P  R  G  Y  C  L  I  I  N  N  H  N  F

CAAAAGCACGGGAGAAAGTGCCCAAACTTCACAGCATTAGGGACAGGAATGGAACACACTTGGATGCAGGGGCTTTGACC 1120

A  K  A  R  E  K  V  P  K  L  H  S  I  R  D  R  N  G  T  H  L  D  A  G  A  L  T

ACGACCTTTGAAGAGCTTCATTTTGAGATCAAGCCCCACCATGACTGCACAGTAGAGCAAATCTATGAGATTTTGAAAAT 1200

T  T  F  E  E  L  H  F  E  I  K  P  H  H  D  C  T  V  E  Q  I  Y  E  I  L  K  I

CTACCAACTCATGGACCACAGTAACATGGACTGCTTCATCTGCTGTATCCTCTCCCATGGAGACAAGGGCATCATCTATG 1280

Y  Q  L  M  D  H  S  N  M  D  C  F  I  C  C  I  L  S  H  G  D  K  G  I  I  Y

GCACTGATGGACAGGAGGCCCCCATCTATGAGCTGACATCTCAGTTCACTGGTTTGAAGTGCCCTTCCCTTGCTGGAAAA 1360

G  T  D  G  Q  E  A  P  I  Y  E  L  T  S  Q  F  T  G  L  K  C  P  S  L  A  G  K

CCCAAAGTGTTTTTTATTCAGGCTTGTCAGGGGGATAACTACCAGAAAGGTATACCTGTTGAGACTGATTCAGAGGAGCA 1440

P  K  V  F  F  I  Q  A  C  Q  G  D  N  Y  Q  K  G  I  P  V  E  T  D  S  E  E  Q

ACCCTATTTAGAAATGGATTTATCATCACCTCAAACGAGATATATCCCGGATGAGGCTGACTTTCTGCTGGGGATGGCCA 1520

P  Y  L  E  M  D  L  S  S  P  Q  T  R  Y  I  P  D  E  A  D  F  L  L  G  M  A

CTGTGAATAACTGTGTTTCCTACCGAAACCCTGCAGAGGGAACCTGGTACATCCAGTCACTTTGCCAGAGCCTGAGAGAG 1600

T  V  N  N  C  V  S  Y  R  N  P  A  E  G  T  W  Y  I  Q  S  L  C  Q  S  L  R  E

CGATGTCCTCGAGGCGATGATATTCTCACCATCCTGACTGAAGTGAACTATGAAGTAAGCAACAAGGATGACAAGAAAAA 1680

R  C  P  R  G  D  D  I  L  T  I  L  T  E  V  N  Y  E  V  S  N  K  D  D  K  K  N

CATGGGGAAACAGATGCCTCAGCCTACTTTCACACTAAGAAAAAAACTTGTCTTCCCTTCTGATTGATGGTGCTATTTTG 1760

M  G  K  Q  M  P  Q  P  T  F  T  L  R  K  K  L  V  F  P  S  D

TTTGTTTTGTTTTGTTTTGTTTTTTTGAGACAGAATCTCGCTCTGTCGCCCAGGCTGGAGTGCAGTGGCGTGATCTCGGC 1840

TCACCGCAAGCTCCGCCTCCCGGGTTCAGGCCATTCTCCTGCT 1883
```

*Fig. 2B*

```
                                                                          Consensus
   F......L......S...L.S...L..LKFL.........K..KLE.
 1 MDPFLV--LLHSVSSSLSSSELTELKFLCLGRVGKRKKLER          human FADD
 1 V-SERE----KL--IDSNLGVQDVENLKFLCIGLVPNKKLEK         Mch4 A
 1 SRN--------LYDIGEQLSEDLASLKFLSLDYIPQRKQEP          Mch5 A
 1 VSLE----RNLLYELSEGIDSENLKDMIFLLKDSLPKTEM--         Mch4 B
 1 VDHLLIRVMLYQISEEVSRSELRSFKELLQEEISKCKLDD           Mch5 B Consensus
   ...LD.F..L......L............L.ELL.........LL..
 39 VOSGLDLFSMLLEONDLEPGHTELLRELLASLRRHDLLRR          human FADD
 38 SSSASDVFEHLLAEDLLSEEDPFFLAELLYIIRQKKLLQH          Mch4 A
 35 IKDALMLFQRLQEKRMLESNLSFLKELLFRINRLDLL--           Mch5 A
 37 --TSLSFLAFLEKQGKIDEDNLTCLEDLCKTVVP-KLLRN          Mch4 B
 41 DMNLLDIEIEMEKRVILGEGKLDILKRVCAQINK-SLLK-          Mch5 B Consensus
   .......
 79 VDDFEA                                            human FADD
 78 LN                                                Mch4 A
 73 ---ITY                                            Mch5 A
 74 IEKYK                                             Mch4 B
 79 -----I                                            Mch5 B
```

*Fig. 3A*

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
      (A) LENGTH: 1700 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 148..1584

(ix) FEATURE:
      (A) NAME/KEY: misc_feature
      (B) LOCATION: 1..1700
      (D) OTHER INFORMATION: /note= "Mch4"

(xi) SEQUENCE DESCRIPTION: SEQ ID NO:1:

```
TGAAGTCTCT TCCCAAGCAA ATGGGAGCTT CTTTGGACCT TGGAGCACAC AGAGGATTCT      60

ACTTTCTTTA AAACTTTGTT TTCAGGCAAT TTCCCTGAGA ACCGTTTACT TCCAGAAGAT     120

TGGTGGAGCT TGATCTGAAG GCTGGCC ATG AAA TCT CAA GGT CAA CAT TGG         171
                              Met Lys Ser Gln Gly Gln His Trp
                                1               5
```

```
TAT TCC AGT TCA GAT AAA AAC TGT AAA GTG AGC TTT CGT GAG AAG CTT      219
Tyr Ser Ser Ser Asp Lys Asn Cys Lys Val Ser Phe Arg Glu Lys Leu
         10                  15                  20

CTG ATT ATT GAT TCA AAC CTG GGG GTC CAA GAT GTG GAG AAC CTC AAG      267
Leu Ile Ile Asp Ser Asn Leu Gly Val Gln Asp Val Glu Asn Leu Lys
25                  30                  35                  40

TTT CTC TGC ATA GGA TTG GTC CCC AAC AAG AAG CTG GAG AAG TCC AGC      315
Phe Leu Cys Ile Gly Leu Val Pro Asn Lys Lys Leu Glu Lys Ser Ser
                    45                  50                  55

TCA GCC TCA GAT GTT TTT GAA CAT CTC TTG GCA GAG GAT CTG CTG AGT      363
Ser Ala Ser Asp Val Phe Glu His Leu Leu Ala Glu Asp Leu Leu Ser
                60                  65                  70

GAG GAA GAC CCT TTC TTC CTG GCA GAA CTC CTC TAT ATC ATA CGG CAG      411
Glu Glu Asp Pro Phe Phe Leu Ala Glu Leu Leu Tyr Ile Ile Arg Gln
            75                  80                  85

AAG AAG CTG CTG CAG CAC CTC AAC TGT ACC AAA GAG GAA GTG GAG CGA      459
Lys Lys Leu Leu Gln His Leu Asn Cys Thr Lys Glu Glu Val Glu Arg
        90                  95                  100

CTG CTG CCC ACC CGA CAA AGG GTT TCT CTG TTT AGA AAC CTG CTC TAC      507
Leu Leu Pro Thr Arg Gln Arg Val Ser Leu Phe Arg Asn Leu Leu Tyr
105                 110                 115                 120

GAA CTG TCA GAA GGC ATT GAC TCA GAG AAC TTA AAG GAC ATG ATC TTC      555
Glu Leu Ser Glu Gly Ile Asp Ser Glu Asn Leu Lys Asp Met Ile Phe
                125                 130                 135

CTT CTG AAA GAC TCG CTT CCC AAA ACT GAA ATG ACC TCC CTA AGT TTC      603
Leu Leu Lys Asp Ser Leu Pro Lys Thr Glu Met Thr Ser Leu Ser Phe
            140                 145                 150

CTG GCA TTT CTA GAG AAA CAA GGT AAA ATA GAT GAA GAT AAT CTG ACA      651
Leu Ala Phe Leu Glu Lys Gln Gly Lys Ile Asp Glu Asp Asn Leu Thr
        155                 160                 165

TGC CTG GAG GAC CTC TGC AAA ACA GTT GTA CCT AAA CTT TTG AGA AAC      699
Cys Leu Glu Asp Leu Cys Lys Thr Val Val Pro Lys Leu Leu Arg Asn
170                 175                 180

ATA GAG AAA TAC AAA AGA GAG AAA GCT ATC CAG ATA GTG ACA CCT CCT      747
Ile Glu Lys Tyr Lys Arg Glu Lys Ala Ile Gln Ile Val Thr Pro Pro
185                 190                 195                 200

GTA GAC AAG GAA GCC GAG TCG TAT CAA GGA GAG GAA GAA CTA GTT TCC      795
Val Asp Lys Glu Ala Glu Ser Tyr Gln Gly Glu Glu Glu Leu Val Ser
                205                 210                 215

CAA ACA GAT GTT AAG ACA TTC TTG GAA GCC TTA CCG AGG GCA GCT GTG      843
Gln Thr Asp Val Lys Thr Phe Leu Glu Ala Leu Pro Arg Ala Ala Val
            220                 225                 230

TAC AGG ATG AAT CGG AAC CAC AGA GGC CTC TGT GTC ATT GTC AAC AAC      891
Tyr Arg Met Asn Arg Asn His Arg Gly Leu Cys Val Ile Val Asn Asn
        235                 240                 245

CAC AGC TTT ACC TCC CTG AAG GAC AGA CAA GGA ACC CAT AAA GAT GCT      939
His Ser Phe Thr Ser Leu Lys Asp Arg Gln Gly Thr His Lys Asp Ala
250                 255                 260

GAG ATC CTG AGT CAT GTG TTC CAG TGG CTT GGG TTC ACA GTG CAT ATA      987
Glu Ile Leu Ser His Val Phe Gln Trp Leu Gly Phe Thr Val His Ile
265                 270                 275                 280

CAC AAT AAT GTG ACG AAA GTG GAA ATG GAG ATG GTC CTG CAG AAG CAG     1035
His Asn Asn Val Thr Lys Val Glu Met Glu Met Val Leu Gln Lys Gln
                285                 290                 295

AAG TGC AAT CCA GCC CAT GCC GAC GGG GAC TGC TTC GTG TTC TGT ATT     1083
Lys Cys Asn Pro Ala His Ala Asp Gly Asp Cys Phe Val Phe Cys Ile
            300                 305                 310

CTG ACC CAT GGG AGA TTT GGA GCT GTC TAC TCT TCG GAT GAG GCC CTC     1131
Leu Thr His Gly Arg Phe Gly Ala Val Tyr Ser Ser Asp Glu Ala Leu
        315                 320                 325
```

```
ATT CCC ATT CGG GAG ATC ATG TCT CAC TTC ACA GCC CTG CAG TGC CCT      1179
Ile Pro Ile Arg Glu Ile Met Ser His Phe Thr Ala Leu Gln Cys Pro
    330                 335                 340

AGA CTG GCT GAA AAA CCT AAA CTC TTT TTC ATC CAG GCC TGC CAA GGT      1227
Arg Leu Ala Glu Lys Pro Lys Leu Phe Phe Ile Gln Ala Cys Gln Gly
345                 350                 355                 360

GAA GAG ATA CAG CCT TCC GTA TCC ATC GAA GCA GAT GCT CTG AAC CCT      1275
Glu Glu Ile Gln Pro Ser Val Ser Ile Glu Ala Asp Ala Leu Asn Pro
                365                 370                 375

GAG CAG GCA CCC ACT TCC CTG CAG GAC AGT ATT CCT GCC GAG GCT GAC      1323
Glu Gln Ala Pro Thr Ser Leu Gln Asp Ser Ile Pro Ala Glu Ala Asp
            380                 385                 390

TTC CTA CTT GGT CTG GCC ACT GTC CCA GGC TAT GTA TCC TTT CGG CAT      1371
Phe Leu Leu Gly Leu Ala Thr Val Pro Gly Tyr Val Ser Phe Arg His
        395                 400                 405

GTG GAG GAA GGC AGC TGG TAT ATT CAG TCT CTG TGT AAT CAT CTG AAG      1419
Val Glu Glu Gly Ser Trp Tyr Ile Gln Ser Leu Cys Asn His Leu Lys
    410                 415                 420

AAA TTG GTC CCA AGA CAT GAA GAC ATC TTA TCC ATC CTC ACT GCT GTC      1467
Lys Leu Val Pro Arg His Glu Asp Ile Leu Ser Ile Leu Thr Ala Val
425                 430                 435                 440

AAC GAT GAT GTG AGT CGA AGA GTG GAC AAA CAG GGA ACA AAG AAA CAG      1515
Asn Asp Asp Val Ser Arg Arg Val Asp Lys Gln Gly Thr Lys Lys Gln
                445                 450                 455

ATG CCC CAG CCT GCT TTC ACA CTA AGG AAA AAA CTA GTA TTC CCT GTG      1563
Met Pro Gln Pro Ala Phe Thr Leu Arg Lys Lys Leu Val Phe Pro Val
            460                 465                 470

CCC CTG GAT GCA CTT TCA ATA TAGCAGAGAG TTTTTGNTGG TTCTTAGACC         1614
Pro Leu Asp Ala Leu Ser Ile
        475

TCAAACGAAT CATTGGNTAT AACCTCCAGC CTCCTGCCCA GCACAGGAAT CGGTGGTCTC    1674

CACCTGTCAT TCTAGAAACA GGAAAC                                         1700

(2) INFORMATION FOR SEQ ID NO:2:

(i) SEQUENCE CHARACTERISTICS:
        (A) LENGTH: 479 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Ser Gln Gly Gln His Trp Tyr Ser Ser Asp Lys Asn Cys
  1               5                  10                  15

Lys Val Ser Phe Arg Glu Lys Leu Leu Ile Ile Asp Ser Asn Leu Gly
                 20                  25                  30

Val Gln Asp Val Glu Asn Leu Lys Phe Leu Cys Ile Gly Leu Val Pro
            35                  40                  45

Asn Lys Lys Leu Glu Lys Ser Ser Ala Ser Asp Val Phe Glu His
     50                  55                  60

Leu Leu Ala Glu Asp Leu Leu Ser Glu Glu Asp Pro Phe Phe Leu Ala
 65                  70                  75                  80

Glu Leu Leu Tyr Ile Ile Arg Gln Lys Lys Leu Leu Gln His Leu Asn
                 85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
```

```
              115                 120                 125
Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
                180                 185                 190

Ala Ile Gln Ile Val Thr Pro Pro Val Asp Lys Glu Ala Glu Ser Tyr
            195                 200                 205

Gln Gly Glu Glu Glu Leu Val Ser Gln Thr Asp Val Lys Thr Phe Leu
    210                 215                 220

Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
                245                 250                 255

Arg Gln Gly Thr His Lys Asp Ala Glu Ile Leu Ser His Val Phe Gln
                260                 265                 270

Trp Leu Gly Phe Thr Val His Ile His Asn Asn Val Thr Lys Val Glu
            275                 280                 285

Met Glu Met Val Leu Gln Lys Gln Lys Cys Asn Pro Ala His Ala Asp
    290                 295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335

His Phe Thr Ala Leu Gln Cys Pro Arg Leu Ala Glu Lys Pro Lys Leu
                340                 345                 350

Phe Phe Ile Gln Ala Cys Gln Gly Glu Glu Ile Gln Pro Ser Val Ser
            355                 360                 365

Ile Glu Ala Asp Ala Leu Asn Pro Glu Gln Ala Pro Thr Ser Leu Gln
    370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415

Gln Ser Leu Cys Asn His Leu Lys Lys Leu Val Pro Arg His Glu Asp
                420                 425                 430

Ile Leu Ser Ile Leu Thr Ala Val Asn Asp Asp Val Ser Arg Arg Val
            435                 440                 445

Asp Lys Gln Gly Thr Lys Lys Gln Met Pro Gln Pro Ala Phe Thr Leu
    450                 455                 460

Arg Lys Lys Leu Val Phe Pro Val Pro Leu Asp Ala Leu Ser Ile
465                 470                 475
```

(2) INFORMATION FOR SEQ ID NO:3:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ix) FEATURE:
        (A) NAME/KEY: CDS (B) LOCATION: 257..1744

(ix) FEATURE:
    (A) NAME/KEY: misc_feature
    (B) LOCATION: 1..1883
    (D) OTHER INFORMATION: /note= "Mch5"

(xi) SEQUENCE DESCRIPTION: SEQ ID NO:3:

```
TGAAGGCTGG TTGTTCAGAC TGAGCTTCCT GCCTGCCTGT ACCCCGCCAA CAGCTTCAGA      60

AGAAGGTGAC TGGTGGCTGC CTGAGGAATA CCAGTGGGCA AGAGAATTAG CATTTCTGGA     120

GCATCTGCTG TCTGAGCAGC CCCTGGGTGC GTCCACTTTC TGGGCACGTG AGGTTGGGCC     180

TTGGCCGCCT GAGCCCTTGA GTTGGTCACT TGAACCTTGG GAATATTGAG ATTATATTCT     240

CCTGCCTTTT AAAAAG ATG GAC TTC AGC AGA AAT CTT TAT GAT ATT GGG         289
              Met Asp Phe Ser Arg Asn Leu Tyr Asp Ile Gly
               1               5                  10

GAA CAA CTG GAC AGT GAA GAT CTG GCC TCC CTC AAG TTC CTG AGC CTG       337
Glu Gln Leu Asp Ser Glu Asp Leu Ala Ser Leu Lys Phe Leu Ser Leu
             15                  20                  25

GAC TAC ATT CCG CAA AGG AAG CAA GAA CCC ATC AAG GAT GCC TTG ATG       385
Asp Tyr Ile Pro Gln Arg Lys Gln Glu Pro Ile Lys Asp Ala Leu Met
         30                  35                  40

TTA TTC CAG AGA CTC CAG GAA AAG AGA ATG TTG GAG GAA AGC AAT CTG       433
Leu Phe Gln Arg Leu Gln Glu Lys Arg Met Leu Glu Glu Ser Asn Leu
     45                  50                  55

TCC TTC CTG AAG GAG CTG CTC TTC CGA ATT AAT AGA CTG GAT TTG CTG       481
Ser Phe Leu Lys Glu Leu Leu Phe Arg Ile Asn Arg Leu Asp Leu Leu
 60                  65                  70                  75

ATT ACC TAC CTA AAC ACT AGA AAG GAG GAG ATG GAA AGG GAA CTT CAG       529
Ile Thr Tyr Leu Asn Thr Arg Lys Glu Glu Met Glu Arg Glu Leu Gln
                 80                  85                  90

ACA CCA GGC AGG GCT CAA ATT TCT GCC TAC AGG TTC CAC TTC TGC CGC       577
Thr Pro Gly Arg Ala Gln Ile Ser Ala Tyr Arg Phe His Phe Cys Arg
             95                 100                 105

ATG AGC TGG GCT GAA GCA AAC AGC CAG TGC CAG ACA CAG TCT GTA CCT       625
Met Ser Trp Ala Glu Ala Asn Ser Gln Cys Gln Thr Gln Ser Val Pro
         110                 115                 120

TTC TGG CGG AGG GTC GAT CAT CTA TTA ATA AGG GTC ATG CTC TAT CAG       673
Phe Trp Arg Arg Val Asp His Leu Leu Ile Arg Val Met Leu Tyr Gln
     125                 130                 135

ATT TCA GAA GAA GTG AGC AGA TCA GAA TTG AGG TCT TTT AAG TTT CTT       721
Ile Ser Glu Glu Val Ser Arg Ser Glu Leu Arg Ser Phe Lys Phe Leu
140                 145                 150                 155

TTG CAA GAG GAA ATC TCC AAA TGC AAA CTG GAT GAT GAC ATG AAC CTG       769
Leu Gln Glu Glu Ile Ser Lys Cys Lys Leu Asp Asp Asp Met Asn Leu
                 160                 165                 170

CTG GAT ATT TTC ATA GAG ATG GAG AAG AGG GTC ATC CTG GGA GAA GGA       817
Leu Asp Ile Phe Ile Glu Met Glu Lys Arg Val Ile Leu Gly Glu Gly
             175                 180                 185

AAG TTG GAC ATC CTG AAA AGA GTC TGT GCC CAA ATC AAC AAG AGC CTG       865
Lys Leu Asp Ile Leu Lys Arg Val Cys Ala Gln Ile Asn Lys Ser Leu
         190                 195                 200

CTG AAG ATA ATC AAC GAC TAT GAA GAA TTC AGC AAA GGG GAG GAG TTG       913
Leu Lys Ile Ile Asn Asp Tyr Glu Glu Phe Ser Lys Gly Glu Glu Leu
     205                 210                 215

TGT GGG GTA ATG ACG ATG TCG GAC TGT CCA AGA GAA CAG GAT AGT GAA       961
Cys Gly Val Met Thr Met Ser Asp Cys Pro Arg Glu Gln Asp Ser Glu
220                 225                 230                 235

TCA CAG ACT TTG GAC AAA GTT TAC CAA ATG AAA AGC AAG CCT CGG GGA      1009
Ser Gln Thr Leu Asp Lys Val Tyr Gln Met Lys Ser Lys Pro Arg Gly
```

-continued

```
                     240                      245                           250
TAC TGT CTG ATC ATC AAC AAT CAC AAT TTT GCA AAA GCA CGG GAG AAA         1057
Tyr Cys Leu Ile Ile Asn Asn His Asn Phe Ala Lys Ala Arg Glu Lys
                255                      260                      265

GTG CCC AAA CTT CAC AGC ATT AGG GAC AGG AAT GGA ACA CAC TTG GAT         1105
Val Pro Lys Leu His Ser Ile Arg Asp Arg Asn Gly Thr His Leu Asp
                270                      275                      280

GCA GGG GCT TTG ACC ACG ACC TTT GAA GAG CTT CAT TTT GAG ATC AAG         1153
Ala Gly Ala Leu Thr Thr Thr Phe Glu Glu Leu His Phe Glu Ile Lys
                285                      290                      295

CCC CAC CAT GAC TGC ACA GTA GAG CAA ATC TAT GAG ATT TTG AAA ATC         1201
Pro His His Asp Cys Thr Val Glu Gln Ile Tyr Glu Ile Leu Lys Ile
300                      305                      310                      315

TAC CAA CTC ATG GAC CAC AGT AAC ATG GAC TGC TTC ATC TGC TGT ATC         1249
Tyr Gln Leu Met Asp His Ser Asn Met Asp Cys Phe Ile Cys Cys Ile
                320                      325                      330

CTC TCC CAT GGA GAC AAG GGC ATC ATC TAT GGC ACT GAT GGA CAG GAG         1297
Leu Ser His Gly Asp Lys Gly Ile Ile Tyr Gly Thr Asp Gly Gln Glu
                335                      340                      345

GCC CCC ATC TAT GAG CTG ACA TCT CAG TTC ACT GGT TTG AAG TGC CCT         1345
Ala Pro Ile Tyr Glu Leu Thr Ser Gln Phe Thr Gly Leu Lys Cys Pro
                350                      355                      360

TCC CTT GCT GGA AAA CCC AAA GTG TTT TTT ATT CAG GCT TGT CAG GGG         1393
Ser Leu Ala Gly Lys Pro Lys Val Phe Phe Ile Gln Ala Cys Gln Gly
                365                      370                      375

GAT AAC TAC CAG AAA GGT ATA CCT GTT GAG ACT GAT TCA GAG GAG CAA         1441
Asp Asn Tyr Gln Lys Gly Ile Pro Val Glu Thr Asp Ser Glu Glu Gln
380                      385                      390                      395

CCC TAT TTA GAA ATG GAT TTA TCA TCA CCT CAA ACG AGA TAT ATC CCG         1489
Pro Tyr Leu Glu Met Asp Leu Ser Ser Pro Gln Thr Arg Tyr Ile Pro
                400                      405                      410

GAT GAG GCT GAC TTT CTG CTG GGG ATG GCC ACT GTG AAT AAC TGT GTT         1537
Asp Glu Ala Asp Phe Leu Leu Gly Met Ala Thr Val Asn Asn Cys Val
                415                      420                      425

TCC TAC CGA AAC CCT GCA GAG GGA ACC TGG TAC ATC CAG TCA CTT TGC         1585
Ser Tyr Arg Asn Pro Ala Glu Gly Thr Trp Tyr Ile Gln Ser Leu Cys
                430                      435                      440

CAG AGC CTG AGA GAG CGA TGT CCT CGA GGC GAT GAT ATT CTC ACC ATC         1633
Gln Ser Leu Arg Glu Arg Cys Pro Arg Gly Asp Asp Ile Leu Thr Ile
                445                      450                      455

CTG ACT GAA GTG AAC TAT GAA GTA AGC AAC AAG GAT GAC AAG AAA AAC         1681
Leu Thr Glu Val Asn Tyr Glu Val Ser Asn Lys Asp Asp Lys Lys Asn
460                      465                      470                      475

ATG GGG AAA CAG ATG CCT CAG CCT ACT TTC ACA CTA AGA AAA AAA CTT         1729
Met Gly Lys Gln Met Pro Gln Pro Thr Phe Thr Leu Arg Lys Lys Leu
                480                      485                      490

GTC TTC CCT TCT GAT TGATGGTGCT ATTTTGTTTG TTTTGTTTTG TTTTGTTTTT         1784
Val Phe Pro Ser Asp
                495

TTGAGACAGA ATCTCGCTCT GTCGCCCAGG CTGGAGTGCA GTGGCGTGAT CTCGGCTCAC       1844

CGCAAGCTCC GCCTCCCGGG TTCAGGCCAT TCTCCTGCT                              1883
```

(2) INFORMATION FOR SEQ ID NO:4:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Ser Asn Leu Ser Phe Leu Lys Glu
        50                  55                  60

Leu Leu Phe Arg Ile Asn Arg Leu Asp Leu Leu Ile Thr Tyr Leu Asn
 65                  70                  75                  80

Thr Arg Lys Glu Glu Met Glu Arg Glu Leu Gln Thr Pro Gly Arg Ala
                85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
    130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190

Lys Arg Val Cys Ala Gln Ile Asn Lys Ser Leu Leu Lys Ile Ile Asn
        195                 200                 205

Asp Tyr Glu Glu Phe Ser Lys Gly Glu Glu Leu Cys Gly Val Met Thr
    210                 215                 220

Met Ser Asp Cys Pro Arg Glu Gln Asp Ser Glu Ser Gln Thr Leu Asp
225                 230                 235                 240

Lys Val Tyr Gln Met Lys Ser Lys Pro Arg Gly Tyr Cys Leu Ile Ile
                245                 250                 255

Asn Asn His Asn Phe Ala Lys Ala Arg Glu Lys Val Pro Lys Leu His
            260                 265                 270

Ser Ile Arg Asp Arg Asn Gly Thr His Leu Asp Ala Gly Ala Leu Thr
        275                 280                 285

Thr Thr Phe Glu Glu Leu His Phe Glu Ile Lys Pro His His Asp Cys
    290                 295                 300

Thr Val Glu Gln Ile Tyr Glu Ile Leu Lys Ile Tyr Gln Leu Met Asp
305                 310                 315                 320

His Ser Asn Met Asp Cys Phe Ile Cys Cys Ile Leu Ser His Gly Asp
                325                 330                 335

Lys Gly Ile Ile Tyr Gly Thr Asp Gly Gln Glu Ala Pro Ile Tyr Glu
            340                 345                 350

Leu Thr Ser Gln Phe Thr Gly Leu Lys Cys Pro Ser Leu Ala Gly Lys
        355                 360                 365

Pro Lys Val Phe Phe Ile Gln Ala Cys Gln Gly Asp Asn Tyr Gln Lys
    370                 375                 380

Gly Ile Pro Val Glu Thr Asp Ser Glu Glu Gln Pro Tyr Leu Glu Met
385                 390                 395                 400

Asp Leu Ser Ser Pro Gln Thr Arg Tyr Ile Pro Asp Glu Ala Asp Phe
```

```
                    405                 410                 415
Leu Leu Gly Met Ala Thr Val Asn Asn Cys Val Ser Tyr Arg Asn Pro
                420                 425                 430

Ala Glu Gly Thr Trp Tyr Ile Gln Ser Leu Cys Gln Ser Leu Arg Glu
                435                 440                 445

Arg Cys Pro Arg Gly Asp Asp Ile Leu Thr Ile Leu Thr Glu Val Asn
                450                 455                 460

Tyr Glu Val Ser Asn Lys Asp Asp Lys Lys Asn Met Gly Lys Gln Met
465                 470                 475                 480

Pro Gln Pro Thr Phe Thr Leu Arg Lys Lys Leu Val Phe Pro Ser Asp
                485                 490                 495
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..19
        (D) OTHER INFORMATION: /note= "t96-pr1"

(xi) SEQUENCE DESCRIPTION: SEQ ID NO:5:

TCAGCCTCGG CAGGAATAC                                    19

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..17
        (D) OTHER INFORMATION: /note= "SK-Zap"

(xi) SEQUENCE DESCRIPTION: SEQ ID NO:6:

CAGGAATTCG GCACGAG                                      17

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..18
        (D) OTHER INFORMATION: /note= "Mch5-pr1"

(xi) SEQUENCE DESCRIPTION: SEQ ID NO:7:

GACAGAGCGA GATTCTGT                                    18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
            (A) NAME/KEY: misc_feature
            (B) LOCATION: 1..18
            (D) OTHER INFORMATION: /note= "Mch5-pr2"

(xi) SEQUENCE DESCRIPTION: SEQ ID NO:8:

GCACCATCAA TCAGAAGG                                                         18

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..18
            (D) OTHER INFORMATION: /note= "Mch5-pr5"

(xi) SEQUENCE DESCRIPTION: SEQ ID NO:9:

CGGGAGATCA TGTCTCAC                                                         18

(2) INFORMATION FOR SEQ ID NO:10:

(i) SEQUENCE CHARACTERISTICS:
            (A) LENGTH: 5 amino acids
            (B) TYPE: amino acid
            (C) STRANDEDNESS:
            (D) TOPOLOGY: linear (xi) SEQUENCE DESCRIPTION: SEQ ID NO:10:

Gln Ala Cys Gln Gly
        1               5

(2) INFORMATION FOR SEQ ID NO:11:

(i) SEQUENCE CHARACTERISTICS:
            (A) LENGTH: 5 amino acids
            (B) TYPE: amino acid
            (C) STRANDEDNESS:
            (D) TOPOLOGY: linear (xi) SEQUENCE DESCRIPTION: SEQ ID NO:11:

Gln Ala Cys Arg Gly
1               5

(2) INFORMATION FOR SEQ ID NO:12:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /note= "Mch5"

(xi) SEQUENCE DESCRIPTION: SEQ ID NO:12:

Arg Asp Arg Asn Gly Thr
1               5

(2) INFORMATION FOR SEQ ID NO:13:

```
    (i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "Mch5"

(xi) SEQUENCE DESCRIPTION: SEQ ID NO:13:

Leu Ser His Gly Asp Lys
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note= "Mch5"

(xi) SEQUENCE DESCRIPTION: SEQ ID NO:14:

Phe Ile Gln Ala Cys Gln Gly Asp Asn
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "Mch5"

(xi) SEQUENCE DESCRIPTION: SEQ ID NO:15:

Val Glu Thr Asp Ser
1               5

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "Mch5"

(xi) SEQUENCE DESCRIPTION: SEQ ID NO:16:
```

```
Asn Cys Val Ser Tyr Arg Asn Pro Ala Glu Gly Thr Trp Tyr Ile
1               5                   10                  15
```

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "Mch4"

(xi) SEQUENCE DESCRIPTION: SEQ ID NO:17:

```
Lys Asp Arg Gln Gly Thr
1               5
```

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "Mch4"

(xi) SEQUENCE DESCRIPTION: SEQ ID NO:18:

```
Leu Thr His Gly Arg Phe
1               5
```

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note= "Mch4"

(xi) SEQUENCE DESCRIPTION: SEQ ID NO:19:

```
Phe Ile Gln Ala Cys Gln Gly Glu Glu
1               5
```

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide (B) LOCATION: 1..5
          (D) OTHER INFORMATION: /note= "Mch4"

(xi) SEQUENCE DESCRIPTION: SEQ ID NO:20:

Ile Glu Ala Asp Ala
1               5

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "Mch4"

(xi) SEQUENCE DESCRIPTION: SEQ ID NO:21:

Gly Tyr Val Ser Phe Arg His Val Glu Glu Gly Ser Trp Tyr Ile
1               5                   10                  15

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "Mch3"

(xi) SEQUENCE DESCRIPTION: SEQ ID NO:22:

Gly Val Arg Asn Gly Thr
1               5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "Mch3"

(xi) SEQUENCE DESCRIPTION: SEQ ID NO:23:

Leu Ser His Gly Glu Glu
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS:
        (D) TOPOLOGY: linear

```
    (ii) MOLECULE TYPE: peptide (ix) FEATURE:
         (A) NAME/KEY: Peptide
         (B) LOCATION: 1..9
         (D) OTHER INFORMATION: /note= "Mch3"

(xi) SEQUENCE DESCRIPTION: SEQ ID NO:24:

Phe Ile Gln Ala Cys Arg Gly Thr Glu
1               5

(2) INFORMATION FOR SEQ ID NO:25:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..5
         (D) OTHER INFORMATION: /note= "Mch3"

(xi) SEQUENCE DESCRIPTION: SEQ ID NO:25:

Ile Gln Ala Asp Ser
1               5

(2) INFORMATION FOR SEQ ID NO:26:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..15
         (D) OTHER INFORMATION: /note= "Mch3"

(xi) SEQUENCE DESCRIPTION: SEQ ID NO:26:

Gly Tyr Tyr Ser Trp Arg Ser Pro Gly Arg Gly Ser Trp Phe Val
1               5                   10                  15

(2) INFORMATION FOR SEQ ID NO:27:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /note= "Mch2"

(xi) SEQUENCE DESCRIPTION: SEQ ID NO:27:

Pro Glu Arg Arg Gly Thr
1               5

(2) INFORMATION FOR SEQ ID NO:28:
```

```
        (i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /note= "Mch2"

(xi) SEQUENCE DESCRIPTION: SEQ ID NO:28:

Leu Ser His Gly Glu Gly
1               5

(2) INFORMATION FOR SEQ ID NO:29:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /note= "Mch2"

(xi) SEQUENCE DESCRIPTION: SEQ ID NO:29:

Ile Ile Gln Ala Cys Arg Gly Asn Gln
1               5

(2) INFORMATION FOR SEQ ID NO:30:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "Mch2"

(xi) SEQUENCE DESCRIPTION: SEQ ID NO:30:

Thr Glu Val Asp Ala
1               5

(2) INFORMATION FOR SEQ ID NO:31:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..15
            (D) OTHER INFORMATION: /note= "Mch2"

(xi) SEQUENCE DESCRIPTION: SEQ ID NO:31:

Gly Tyr Tyr Ser His Arg Glu Thr Val Asn Gly Ser Trp Tyr Ile
```

```
1               5              10             15
```

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "CPP32"

(xi) SEQUENCE DESCRIPTION: SEQ ID NO:32:

```
Thr Ser Arg Ser Gly Thr
1               5
```

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "CPP32"

(xi) SEQUENCE DESCRIPTION: SEQ ID NO:33:

```
Leu Ser His Gly Glu Glu
1               5
```

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note= "CPP32"

(xi) SEQUENCE DESCRIPTION: SEQ ID NO:34:

```
Ile Ile Gln Ala Cys Arg Gly Thr Glu
1               5
```

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5

(D) OTHER INFORMATION: /note= "CPP32"

(xi) SEQUENCE DESCRIPTION: SEQ ID NO:35:

Ile Glu Thr Asp Ser
1               5

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "CPP32"

(xi) SEQUENCE DESCRIPTION: SEQ ID NO:36:

Gly Tyr Tyr Ser Trp Arg Asn Ser Lys Asp Gly Ser Trp Phe Ile
1               5                   10                  15

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "CED-3"

(xi) SEQUENCE DESCRIPTION: SEQ ID NO:37:

Pro Thr Arg Asn Gly Thr
1               5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "CED-3"

(xi) SEQUENCE DESCRIPTION: SEQ ID NO:38:

Leu Ser His Gly Glu Glu
1               5

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS:
        (D) TOPOLOGY: linear

```
     (ii) MOLECULE TYPE: peptide (ix) FEATURE:
          (A) NAME/KEY: Peptide
          (B) LOCATION: 1..9
          (D) OTHER INFORMATION: /note= "CED-3"

(xi) SEQUENCE DESCRIPTION: SEQ ID NO:39:

Phe Val Gln Ala Cys Arg Gly Glu Arg
1               5

(2) INFORMATION FOR SEQ ID NO:40:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Peptide
          (B) LOCATION: 1..5
          (D) OTHER INFORMATION: /note= "CED-3"

(xi) SEQUENCE DESCRIPTION: SEQ ID NO:40:

Asp Ser Val Asp Gly
1               5

(2) INFORMATION FOR SEQ ID NO:41:

(i) SEQUENCE CHARACTERISTICS:
          (A) LENGTH: 15 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Peptide
          (B) LOCATION: 1..15
          (D) OTHER INFORMATION: /note= "CED-3"

(xi) SEQUENCE DESCRIPTION: SEQ ID NO:41:

Asp Asn Val Ser Trp Arg His Pro Thr Met Gly Ser Val Phe Ile
1               5                   10                  15

(2) INFORMATION FOR SEQ ID NO:42:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Peptide
          (B) LOCATION: 1..6
          (D) OTHER INFORMATION: /note= "ICE"

(xi) SEQUENCE DESCRIPTION: SEQ ID NO:42:

Pro Arg Arg Thr Gly Ala
1               5

(2) INFORMATION FOR SEQ ID NO:43:

(i) SEQUENCE CHARACTERISTICS:
```

(A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "ICE"

(xi) SEQUENCE DESCRIPTION: SEQ ID NO:43:

Met Ser His Gly Ile Arg
1               5

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note= "ICE"

(xi) SEQUENCE DESCRIPTION: SEQ ID NO:44:

Ile Ile Gln Ala Cys Arg Gly Asp Ser
1               5

(2) INFORMATION FOR SEQ ID NO:45:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "ICE"

(xi) SEQUENCE DESCRIPTION: SEQ ID NO:45:

Trp Phe Lys Asp Ser
1               5

(2) INFORMATION FOR SEQ ID NO:46:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "ICE"

(xi) SEQUENCE DESCRIPTION: SEQ ID NO:46:

Asp Asn Val Ser Trp Arg His Pro Thr Met Gly Ser Val Phe Ile
1               5                  10                  15

(2) INFORMATION FOR SEQ ID NO:47:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Peptide
      (B) LOCATION: 1..6
      (D) OTHER INFORMATION: /note= "TX"

(xi) SEQUENCE DESCRIPTION: SEQ ID NO:47:

Pro Pro Arg Asn Gly Ala
1               5

(2) INFORMATION FOR SEQ ID NO:48:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Peptide
      (B) LOCATION: 1..6
      (D) OTHER INFORMATION: /note= "TX"

(xi) SEQUENCE DESCRIPTION: SEQ ID NO:48:

Met Ser His Gly Ile Leu
1               5

(2) INFORMATION FOR SEQ ID NO:49:

(i) SEQUENCE CHARACTERISTICS:
      (A) LENGTH: 9 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Peptide
      (B) LOCATION: 1..9
      (D) OTHER INFORMATION: /note= "TX"

(xi) SEQUENCE DESCRIPTION: SEQ ID NO:49:

Ile Val Gln Ala Cys Arg Gly Ala Asn
1               5

(2) INFORMATION FOR SEQ ID NO:50:

(i) SEQUENCE CHARACTERISTICS:
      (A) LENGTH: 5 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Peptide
      (B) LOCATION: 1..5
      (D) OTHER INFORMATION: /note= "TX"

(xi) SEQUENCE DESCRIPTION: SEQ ID NO:50:

Trp Val Lys Asp Ser
1               5

(2) INFORMATION FOR SEQ ID NO:51:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..15
         (D) OTHER INFORMATION: /note= "TX"

(xi) SEQUENCE DESCRIPTION: SEQ ID NO:51:

His Asn Val Ser Trp Arg Asp Ser Thr Met Gly Ser Ile Phe Ile
1               5                  10                  15

(2) INFORMATION FOR SEQ ID NO:52:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /note= "ICErelIII"

(xi) SEQUENCE DESCRIPTION: SEQ ID NO:52:

Pro Ala Arg Asn Gly Ala
1               5

(2) INFORMATION FOR SEQ ID NO:53:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /note= "ICErelIII"

(xi) SEQUENCE DESCRIPTION: SEQ ID NO:53:

Met Ser His Gly Ile Leu
1               5

(2) INFORMATION FOR SEQ ID NO:54:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /note= "ICErelIII"

(xi) SEQUENCE DESCRIPTION: SEQ ID NO:54:

Ile Val Gln Ala Cys Arg Gly Glu Lys
1               5

(2) INFORMATION FOR SEQ ID NO:55:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "ICErelIII"

(xi) SEQUENCE DESCRIPTION: SEQ ID NO:55:

Trp Val Arg Asp Ser
1               5

(2) INFORMATION FOR SEQ ID NO:56:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..15
            (D) OTHER INFORMATION: /note= "ICErelIII"

(xi) SEQUENCE DESCRIPTION: SEQ ID NO:56:

His Asn Val Ser Trp Arg Asp Arg Thr Arg Gly Ser Ile Phe Ile
1               5                   10                  15

(2) INFORMATION FOR SEQ ID NO:57:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /note= "ICH-1"

(xi) SEQUENCE DESCRIPTION: SEQ ID NO:57:

Glu Phe Arg Ser Gly Gly
1               5

(2) INFORMATION FOR SEQ ID NO:58:

(i) SEQUENCE CHARACTERISTICS:
            (A) LENGTH: 6 amino acids

```
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /note= "ICH-1"

(xi) SEQUENCE DESCRIPTION: SEQ ID NO:58:

Leu Ser His Gly Val Glu
1               5

(2) INFORMATION FOR SEQ ID NO:59:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /note= "ICH-1"

(xi) SEQUENCE DESCRIPTION: SEQ ID NO:59:

Phe Ile Gln Ala Cys Arg Gly Asp Glu
1               5

(2) INFORMATION FOR SEQ ID NO:60:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "ICH-1"

(xi) SEQUENCE DESCRIPTION: SEQ ID NO:60:

Asp Gln Gln Asp Gly
1               5

(2) INFORMATION FOR SEQ ID NO:61:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..15
            (D) OTHER INFORMATION: /note= "ICH-1"

(xi) SEQUENCE DESCRIPTION: SEQ ID NO:61:

Gly Thr Ala Ala Met Arg Asn Thr Lys Arg Gly Ser Trp Tyr Ile
1               5                   10                  15
```

(2) INFORMATION FOR SEQ ID NO:62:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:62:

```
CCTACAGGAT CCACTTCTGC CGCATGAGC                                    29
```

(2) INFORMATION FOR SEQ ID NO:63:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:63:

```
ACTCCTCCCC TTTGCTGAAT TCTTAATAGT CGT                               33
```

(2) INFORMATION FOR SEQ ID NO:64:

(i) SEQUENCE CHARACTERISTICS:
        (A) LENGTH: 84 amino acids
        (B) TYPE: amino acid
        (C) STRANDEDNESS:
        (D) TOPOLOGY: linear (ix) FEATURE:
        (A) NAME/KEY: Peptide
        (B) LOCATION: 1..84
        (D) OTHER INFORMATION: /note= "human FADD"

(xi) SEQUENCE DESCRIPTION: SEQ ID NO:64:

```
Met Asp Pro Phe Leu Val Leu Leu His Ser Val Ser Ser Leu Ser
1               5                  10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Glu Pro Gly His Thr Glu Leu Leu Arg
    50                  55                  60

Glu Leu Leu Ala Ser Leu Arg Arg His Asp Leu Leu Arg Arg Val Asp
65                  70                  75                  80

Asp Phe Glu Ala
```

(2) INFORMATION FOR SEQ ID NO:65:

(i) SEQUENCE CHARACTERISTICS:
        (A) LENGTH: 79 amino acids
        (B) TYPE: amino acid
        (C) STRANDEDNESS:
        (D) TOPOLOGY: linear (ix) FEATURE:
        (A) NAME/KEY: Peptide
        (B) LOCATION: 1..79
        (D) OTHER INFORMATION: /note= "Mch4 A"

(xi) SEQUENCE DESCRIPTION: SEQ ID NO:65:

```
Val Ser Phe Arg Glu Lys Leu Leu Ile Ile Asp Ser Asn Leu Gly Val
1               5                  10                  15

Gln Asp Val Glu Asn Leu Lys Phe Leu Cys Ile Gly Leu Val Pro Asn
```

```
                  20                  25                  30
Lys Lys Leu Glu Lys Ser Ser Ala Ser Asp Val Phe Glu His Leu
            35                  40                  45

Leu Ala Glu Asp Leu Leu Ser Glu Glu Asp Pro Phe Phe Leu Ala Glu
 50                  55                  60

Leu Leu Tyr Ile Ile Arg Gln Lys Lys Leu Leu Gln His Leu Asn
 65                  70                  75
```

(2) INFORMATION FOR SEQ ID NO:66:

(i) SEQUENCE CHARACTERISTICS:
        (A) LENGTH: 75 amino acids
        (B) TYPE: amino acid
        (C) STRANDEDNESS:
        (D) TOPOLOGY: linear (ix) FEATURE:
        (A) NAME/KEY: Peptide
        (B) LOCATION: 1..75
        (D) OTHER INFORMATION: /note= "Mch5 A"

(xi) SEQUENCE DESCRIPTION: SEQ ID NO:66:

```
Ser Arg Asn Leu Tyr Asp Ile Gly Glu Gln Leu Asp Ser Glu Asp Leu
 1               5                  10                  15

Ala Ser Leu Lys Phe Leu Ser Leu Asp Thr Ile Pro Gln Arg Lys Gln
            20                  25                  30

Glu Pro Ile Lys Asp Ala Leu Met Leu Phe Gln Arg Leu Gln Glu Lys
            35                  40                  45

Arg Met Leu Glu Glu Ser Asn Leu Ser Phe Leu Lys Glu Leu Leu Phe
 50                  55                  60

Arg Ile Asn Arg Leu Asp Leu Leu Ile Thr Tyr
 65                  70                  75
```

(2) INFORMATION FOR SEQ ID NO:67:

(i) SEQUENCE CHARACTERISTICS:
        (A) LENGTH: 78 amino acids
        (B) TYPE: amino acid
        (C) STRANDEDNESS:
        (D) TOPOLOGY: linear (ix) FEATURE:
        (A) NAME/KEY: Peptide
        (B) LOCATION: 1..78
        (D) OTHER INFORMATION: /note= "Mch4 B"

(xi) SEQUENCE DESCRIPTION: SEQ ID NO:67:

```
Val Ser Leu Phe Arg Asn Leu Leu Tyr Glu Leu Ser Glu Gly Ile Asp
 1               5                  10                  15

Ser Glu Asn Leu Lys Asp Met Ile Phe Leu Leu Lys Asp Ser Leu Pro
            20                  25                  30

Lys Thr Glu Met Thr Ser Leu Ser Phe Leu Ala Phe Leu Glu Lys Gln
            35                  40                  45

Gly Lys Ile Asp Glu Asp Asn Leu Thr Cys Leu Glu Asp Leu Cys Lys
            50                  55                  60

Thr Val Val Pro Lys Leu Leu Arg Asn Ile Glu Lys Tyr Lys
 65                  70                  75
```

(2) INFORMATION FOR SEQ ID NO:68:

(i) SEQUENCE CHARACTERISTICS:
        (A) LENGTH: 79 amino acids
        (B) TYPE: amino acid (C) STRANDEDNESS:
        (D) TOPOLOGY: linear (ix) FEATURE:
        (A) NAME/KEY: Peptide
        (B) LOCATION: 1..79
        (D) OTHER INFORMATION: /note= "Mch5 B"

(xi) SEQUENCE DESCRIPTION: SEQ ID NO:68:

Val Asp His Leu Leu Ile Arg Val Met Leu Tyr Gln Ile Ser Glu Glu
1               5                   10                  15

Val Ser Arg Ser Glu Leu Arg Ser Phe Lys Phe Leu Leu Gln Glu Glu
            20                  25                  30

Ile Ser Lys Cys Lys Leu Asp Asp Asp Met Asn Leu Leu Asp Ile Phe
        35                  40                  45

Ile Glu Met Glu Lys Arg Val Ile Leu Gly Glu Gly Lys Leu Asp Ile
    50                  55                  60

Leu Lys Arg Val Cys Ala Gln Ile Asn Lys Ser Leu Leu Lys Ile
65                  70                  75

(2) INFORMATION FOR SEQ ID NO:69:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:69:

Gly Ser Trp Phe Ile
1               5

(2) INFORMATION FOR SEQ ID NO:70:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:70:

Gly Ser Trp Tyr Ile
1               5

(2) INFORMATION FOR SEQ ID NO:71:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:71:

Asp Glu Val Asp
1

(2) INFORMATION FOR SEQ ID NO:72:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:72:

Tyr Val Ala Asp

```
(2) INFORMATION FOR SEQ ID NO:73:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:73:

Ile Glu Thr Asp Ser
1               5

(2) INFORMATION FOR SEQ ID NO:74:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:74:

Ile Gln Ala Asp Ala
1               5

(2) INFORMATION FOR SEQ ID NO:75:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:75:

Ile Glu Ala Asp Ala
1               5
```

MCH4 AND MCH5, APOPTOTIC PROTEASE, NUCLEIC ACIDS ENCODING AND METHODS OF USE

CROSS-REFERENCE TO RELATED APPLICATIONS

This application is a continuation of pending U.S. patent application Ser. No. 08/882,429, filed Jun. 25, 1997, now abandoned; which application is a continuation of U.S. patent application Ser. No. 08/665,220 filing date Jun. 14, 1996, now issued as U.S. Pat. No. 5,786,173; which application is a continuation-in-part of U.S. patent application Ser. No.08/618,408, filing date Mar. 19, 1996, now issued as U.S. Pat. No. 5,851,815.

STATEMENT OF GOVERNMENT INTEREST

This invention was made with government support under grants AI 35035-01 from the National Institutes of Health. Accordingly, the government has certain rights in this invention.

TECHNICAL FIELD

Throughout this application various publications are referenced within parentheses. The disclosure of these publications in their entireties are hereby incorporated by reference in this application in order to more fully describe the state of the art to which this invention pertains.

BACKGROUND OF THE INVENTION

The present invention relates generally to apoptosis or, programmed cell death, and more particularly, to novel aspartate-specific cysteine proteases which can be used to modulate apoptosis for the therapeutic treatment of human diseases.

Apoptosis is a normal physiological process of cell death that plays a critical role in the regulation of tissue homeostasis by ensuring that the rate of new cell accumulation produced by cell division is offset by a commensurate rate of cell loss due to death. It has now become clear that disturbances in apoptosis, also referred to as physiological cell death or progranuned cell death, that prevent or delay normal; cell turnover can be just a important to the pathogenesis of diseases as are known abnormalities in the regulation of proliferation and the cell cycle. Like cell division, which is controlled through complex interactions between cell cycle regulatory proteins, apoptosis is similarly regulated under normal circumstances by the interaction of gene products that either induce or inhibit cell death.

The stimuli which regulate the function of these apoptotic gene products include both extracellular and intracellular signals. Either the presence or removal of a particular stimuli can be sufficient to evoke a positive or negative apoptotic signal. For example, physiological stimuli that prevent or inhibit apoptosis include, for example, growth factors, extracellular matrix, CD40 ligand, viral gene products neutral amino acids, zinc, estrogen and androgens. In contrast, stimuli which promote apoptosis include growth factors such as tumor necrosis factor (TNF), Fas, and transforming growth factor β (TGFβ), neurotransmitters, growth withdrawal, loss of extracellular matrix attachment, intracellular calcium and glucocorticoids, for example. Other stimuli, including those of environmental and pathogenetic origins, also exist which can either induce or inhibit programmed cell death. Although apoptosis is mediated by diverse signals and complex interactions of cellular gene products, the results of these interactions ultimately feed into a cell death pathway that is evolutionarily conserved between humans and invertebrates.

Several gene products which modulate the apoptotic process have now been identified. Although these products can in general be separated into two basic categories, gene products from each category can function to either inhibit or induce programmed cell death. One family of gene products are those which are members of the Bcl-2 family of proteins. Bcl-2, is the best characterized member of this family and inhibits apoptosis when overexpressed in cells. Other members of this gene family include, for example, Bax, Bak, Bcl-$x_L$, Bcl-$x_S$, and Bad. While some of these proteins can prevent apoptosis others augment apoptosis (e.g., Bcl-$x_S$ and Bak, respectively.)

A second family of gene products, the aspartate-specific cysteine proteases (ASCPs), are related genetically to the *C. elegans* ced-3 gene product which was initially shown to be required for programmed cell death in the roundworm, *C. elegans*. The ASCPs family of proteases include human ICE (interleukin-1-β converting enzyme), ICH-$1_L$, ICH-$1_S$, CPP32, Mch2, Mch3, ICH-2 and $ICE_{rel}$-III. Among the common features of these gene products is that 1) they are cysteine proteases with specificity for substrate cleavage at Asp-x bonds, 2) they share a conserved pentapeptide sequence (QACRG) SEQ ID NO:11 within the active site and 3) they are synthesized as proenzymes that require proteolytic cleavage at specific aspartate residues for activation of protease activity. Cleavage of the proenzyme produces two polypeptide protease subunits of approximately 20 kD (p20) and 10 kD (p10) which, in the case of ICE, combine non-covalently to form a tetramer comprised of two p20:p10 heterodimers. Although these proteases, when expressed in cells, induce cell death, several alternative structural forms of these proteases, such as ICEδ, ICEε, ICH-$1_S$ and Mch2β, actually function to inhibit apoptosis.

In addition to the Bcl-2 and ASCP gene families which play a role in apoptosis in mammalian cells, it has become increasingly apparent that other gene products exist which are important in mammalian cell death and which have yet to be identified. For example, in addition to Ced-3, another *C. elegans* gene known as Ced-4 exists which is also required for programmed cell death in *C. elegans*. However, mammalian homologies of this protein remain elusive and have not yet been identified. Further, it is ambiguous as to whether other genes exist which belong to either of the above two apoptotic gene families or what role they may play in the programmed cell death pathway. Finally, it is unclear what the physiological control mechanisms are which regulate programmed cell death or how the cell death pathways interact with other physiological processes within the organism. For example, recently it has been suggested that the cytotoxic T-lymphocytes mediate their destructive function by inducing apoptosis in their target cells.

Apoptosis functions in maintaining tissue homeostasis in a range of physiological processes such as embryonic development, immune cell regulation and normal cell turnover. Therefore, the dysfunction, or loss of regulated apoptosis can lead to a variety of pathological disease states. For example, the loss of apoptosis can lead to the pathological accumulation of self-reactive lymphocytes such as that occurring with many autoimmune diseases. Inappropriate loss of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can change the natural progression of many of these diseases.

Thus, there exists a need to identify new apoptosis genes and their gene products and for methods of modulating this process for the therapeutic treatment of human diseases. The present invention satisfied this need and provides related advantages as well.

SUMMARY OF THE INVENTION

The invention provides an isolated gene encoding Mch4 or an isolated gene encoding Mch5 as well as functional fragments thereof. Also provided are isolated nucleic acid sequences encoding Mch4 or Mch5 or functional fragment thereof. The gene or nucleic acid sequences can be single or double stranded nucleic acids corresponding to coding or non-coding strands of the Mch4 or Mch5 nucleotide sequences. Also provided are genes and nucleic acids encoding functional fragments such as the FADD-like domains Mch4A, Mch4B, or Mch5A and Mch5B. Isolated Mch4 or Mch5 polypeptides or functional fragments thereof including the FADD-like domains Mch4A, Mch4B, Mch5A and Mch5B are also provided.

BRIEF DESCRIPTION OF THE DRAWINGS

FIG. 1 shows the nucleotide and predicted amino acid sequence of Mch4 (SEQ ID NOS:1 and 2, respectively).

FIG. 2 shows the nucleotide and predicted amino acid sequences of Mch5 (SEQ ID NOS:3 and 4, respectively).

DETAILED DESCRIPTION OF THE INVENTION

Figure 3B:
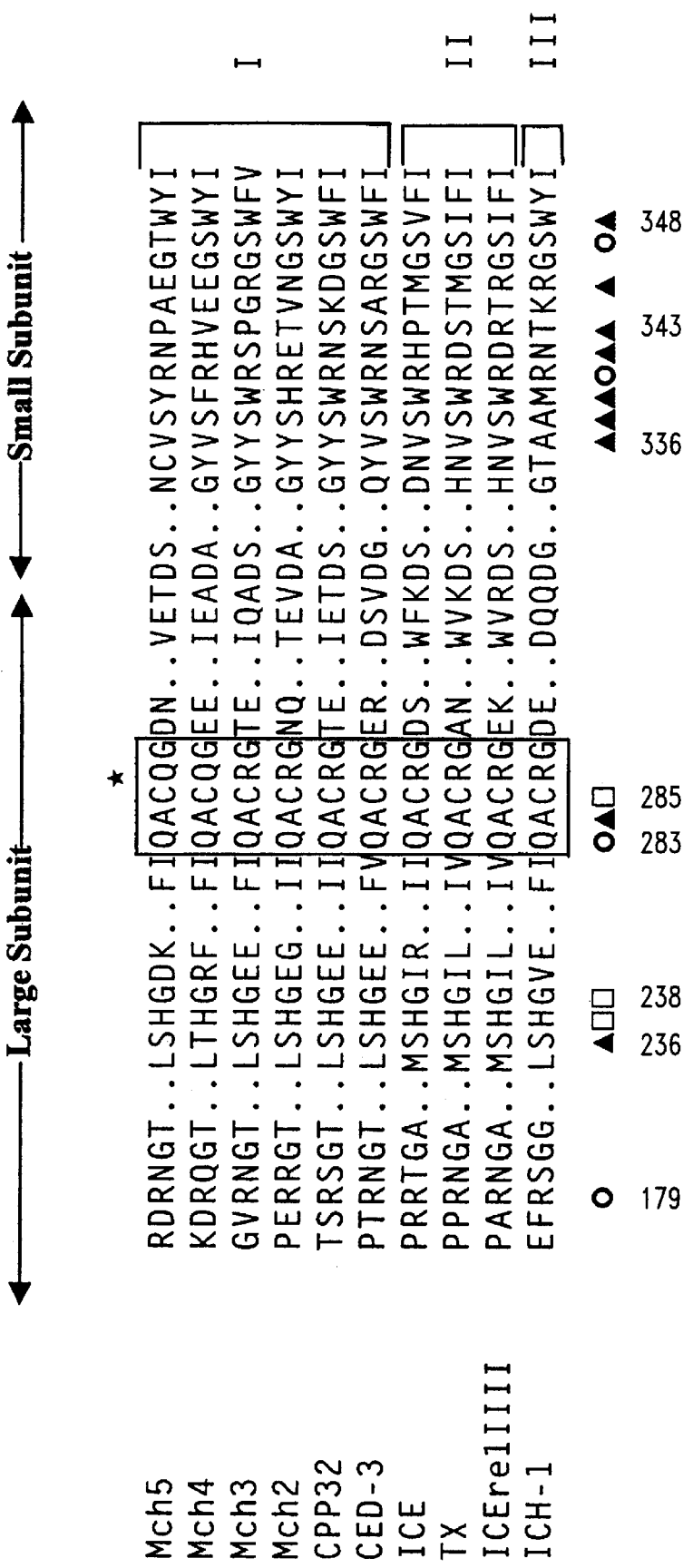
FIG. 3 shows the amino acid sequences of Mch4 and Mch5 and their homology to other ASCP sequences. (A) Colinear alignment of human FADD SEQ ID NO:64 with the two FADD-like domains in both Mchk4 and Mch5. These domains have been denoted as Mch4A (amino acid residues 18–105), SEQ ID NO:65 Mch4B (amino acid 112–189), SEQ ID NOS:66 Mch5A (amino acid 4–77) SEQ ID NO:67 and Mch5B (amino acid 128–205)SEQ ID NO:68. The first domain of Mch4 (Mch4A) has the highest homology to the N-terminal 79 amino acid long FADD (gb accession #U24231) death effector domain (37% identity, 57% similarity) than the second domain (Mch4B) 22% identity, 53% similarity). Mch4A also shows high homology to PEA-15 (gb accession #X86694) and KIAA0179 (gb accession #D80001) proteins. Mch4B shows some homology to SRB7 (gb accession #U46837) and yeast cdc4 (gb accession #Z45255) proteins. (B) Multiple sequence alignment of all known human ASCPs and the nematode Ced-3 ASCP. The active site pentapeptide QACRG/QACQG SEQ ID NO:11 and 10 respecttively is boxed. Based on crystal structure of ICE, the numbered residues within the ICE sequence are involved in catalysis (open boxes), and binding the substrate-carboxylate of PI Asp (open circles). The residue adjacent to the substrate P2–P4 amino acids are indicated by closed triangles. D/X indicates known and potential processing sites between the small and large subunits of ASCPs. The Roman numbers on the right indicate the three ASCP-subfamilies; the Ced-like subfamily (I), the ICE-like subfamily (II) and the NEdd2/Ich-1 subfamily (III). The asterisk indicates the nonconservative Arg to Gln substitution in Mch4 and Mch5.

This invention is directed to novel cell death specific proteases termed Mch4 and Mch5. These proteases are members of the aspartate-specific cysteine protease (ASCP) family of proteases which includes, for example, ICE, ICH-$1_L$, ICH-$1_S$, CPP32, Mch2, Mch3, ICH-2 and ICE$_{rel}$- III. Similar to other ASCPS, Mch4, and Mch5 are synthesized as a larger proenzyme and become active following proteolytic cleavage into two subunits; large subunit of approximately 17–27 kD and small subunit of approximately 10–12 kD. The two subunits form heterodimers which associate with each other into an active complex. Substrate specificity uniquely requires an Asp residue in the P1 position of the substrate binding site with a small, preferably hydrophobic residue in the P1' position. In addition, the N-terminus of both Mch4 and Mch5 contain FADD-like death effector domains indicating their interaction with FADD. This interaction further indicates that through these FADD-like domains, Mch4 and Mch5 function in the fas mediated apoptotic pathway.

In one embodiment, the invention is directed to nucleic acids encoding the apoptotic cysteine protease Mch4 or Mch5. The nucleic acids are used to produce recombinant Mch4 or Mch5 proteases, whose activity can be measured emzymatically. The recombinant polypeptides are used to screen for Mch4 or Mch5 inhibitory compounds. Mch4 or Mch5 inhibiting compounds include those which inhibit protease activity as well as compounds which inhibit Mch4 or Mch5 binding to other polypeptides through FADD-like domains. Such pharmaceutical compounds are useful for the treatment or prevention of diseases which are characterized by apoptotic cell death. Alternatively, the Mch4 or Mch5 polypeptides can be used to screen for pharmaceutical compounds which activate or act as agonists of Mch4 or Mch5 such as by inducing cleavage of the proenzyme into its active subunits or altering polypeptide interactions through their FADD-like domains. Such compounds are useful for the treatment or prevention of diseases which are characterized by the loss of apoptotic cell death.

As used herein, the term "substantially" when referring to Mch4 or Mch5 nucleotide or amino acid sequence is intended to refer to the degree to which two sequences of between about 15–30 or more nucleotides in length, are identical or similar so as to be considered by those skilled in the art to be functionally equivalent. For example, the Mch4 or Mch5 nucleic acids of the invention have a nucleotide sequence substantially the same as that shown in FIGS. 1 and 2 and as SEQ ID NOS:1 and 3, respectively. Thus, if a second sequence is substantially the same as that shown in SEQ ID NOS:1 and 3, then it is considered functionally equivalent by those skilled in the art. Methods for sequence comparisons and determinations of similarity are well known and routine within the art.

Functionally equivalent nucleic acid sequences include, for example, sequences that are related, but different and encode the same Mch4 or Mch5 polypeptide due to the degeneracy of the genetic code as well as sequences that are related, but different and encode a different Mch4 or Mch5 polypeptide that exhibits similar functional activity. In both cases, the nucleic acids encode functionally equivalent gene products. Functional fragments of Mch4 or Mch5 encoding nucleic acids such as oligonucleotides, polyoligonucleotides, primers and the like are also considered to be within the definition of the term and the invention as claimed. Functional equivalency is also relevant to Mch4 or Mch5 nucleic acids which do not encode gene products, for example, but instead are functional elements in and of themselves. Specific examples of such functional nucleic acids include, for example, promoters, enhancers and other gene expression regulatory elements.

Mch4 or Mch5 polypeptides of the invention have an amino acid sequence substantially similar to that shown in FIGS. 1, 2, and 3 and in SEQ ID NOS:2 and 4, respectively. Functionally equivalent Mch4 amino acid sequences similarly includes, for example, related, but different sequences so long as the different polypeptide exhibits at least one functional activity of Mch4 or Mch5. Such related, but different polypeptide include, for example, substitutions of conserved and non-essential amino acids. Fragments and functional domains of Mch4 or Mch5 are similarly included within the definition of the term and the claimed invention.

Therefore, it is understood that limited modifications may be made without destroying the biological function of the Mch4 or Mch5 polypeptide and that only a portion of the entire primary structure may be required in order to effect activity. For example, minor modifications of the Mch4 or Mch5 amino acid sequences (SEQ ID NOS:2 and 4) which do not destroy their activity also fall within the definition of Mch4 or Mch5 and within the definition of the polypeptide claimed as such. Also, for example, genetically engineered fragments of Mch4 or Mch5 either alone or fused to heterologous proteins such as fusion proteins that retain measurable enzymatic or other biological activity fall within the definition of the polypeptide claimed as such.

It is understood that minor modifications of primary amino acid sequence may result in polypeptides which have substantially equivalent or enhanced function as compared to the sequences set forth in FIGS. 1 and 2 (SEQ ID NOS 2 and 4). These modifications may be deliberate, as through site-directed mutagenesis, or may be accidental such as through mutation in hosts which are Mch4 or Mch5 producers. All of these modifications are included as long as Mch4 or Mch5 biological function is retained. Further, various molecules can be attached to Mch4 or Mch5, for example, other proteins, carbohydrates, lipids, or chemical moieties. Such modification are included within the definition of Mch4 or Mch5 polypeptides.

The invention provides a gene encoding Mch4 or Mch5, or fragment thereof. The invention also provides an isolated nucleic acid sequence encoding Mch4 or Mch5, or fragment thereof. The gene and nucleic acid sequences encode substantially the sequence as shown in SEQ ID NOS:1 and 3. Fragments of the gene or nucleic acid sequence are provided which comprise single or double stranded nucleic acids having substantially the sequences shown in SEQ ID NOS:1 and 3.

The Mch4 or Mch5 nucleic acids of the present invention were identified and isolated by a novel approach of searching a human database of expressed sequence tags (ESTs) under various stringencies to identify potential new sequence fragments which may have homology to the ICE family of cysteine proteases. As described below, such a search identified the Mch4 and Mch5 nucleic acids of the present invention and also resulted in the reclassification of the cell death protease family. Previously these proteases were referred to as the ICE-family of proteases and thus the initial search criteria was directed to "ICE family" of cell death proteases. However, with the identification of Mch4 and Mch5, the proteases can now be divided into three subfamilies referred to herein as the Ced-like, ICE-like and Nedd2/ICH-1-like subfamilies of cell death proteases (see FIG. 3B).

In regard to the search for potential new sequences having homology to the previously referred to ICE family of proteases, novel sequences identified from the search as having homology to the ICE family of cell death proteases are then used to design primers for attempting PCR amplification and cloning of the actual cDNA. The second primer for the amplification is designed to encompass homologous regions in nucleic acid sequences that encode know ICE protease family members. In this specific case, the primer was directed to the GSWFI/GSWYI SEQ ID NOS:69 and 70 respectively pentapeptide sequence that is conserved in a number of the ICE/Ced-3 family of proteases. The primer designs should take into account the predicted strandedness of both the EST sequence primer and the known primer. Thus, only if the homology search and primer hybridization conditions are successfully determined, will such an approach allow PCR amplification of a fragment of the putative novel protease cDNA.

As searching a genetic data base will yield homologous sequence matches to any query nucleotide sequence, additional criteria must be used to identify the authentic ICE subfamily homologue from among the non-specific homology matches. ICE family members share the highest degree of homology in the active site and catalytically important amino acid residues. A given EST returned by the search may not include one of these highly homologous sites, but rather, may only include a region within the protease with cryptic homology. Confirming an EST as a novel ICE protease involves translation of all the positive EST hits in three different reading frames and subsequent identification of conservative active site or catalytically important amino acid sequence motifs. Then, using conventional cDNA cloning, a full length cDNA of the putative novel protease can be obtained and 1) analyzed for overall structural homology to ICE family members, 2) recombinantly expressed and analyzed for cysteine protease activity, and 3) analyzed for the induction of programmed cell death by heterologous expression of the cDNA in appropriate cells.

Alternative methods than that described above for isolating Mch4 or Mch5 encoding nucleic acids can similarly be employed. For example, using the teachings described herein, those skilled in the art can routinely isolate and manipulate Mch4 or Mch5 nucleic acids using methods well known in the art. All that is necessary is the sequence of the Mch4 or Mch5 encoding nucleic acids (FIGS. 1 and 2 and SEQ ID NOS:1 and 3) or their amino acids sequences (FIGS. 1 and 2 and SEQ ID NOS:2 and 4). Such methods include, for example, screening a cDNA or genomic library by using synthetic oligonucleotides, nucleotides, nucleic acid fragments or primers as hybridization probes. Alternatively, antibodies to the Mch4 or Mch5 amino acid sequence or fragments thereof can be generated and used to screen an expression library to isolate Mch4 or Mch5 encoding nucleic acids. Other binding reagents to Mch4 or Mch5 polypeptides can similarly be used to isolate Mch4 or Mch5 polypeptides having substantially the amino acid sequence show in FIGS. 1 and 2. Similarly, substrate reagents such as non-cleavable peptide analogues of cysteine proteases and FADD-like domain binding polypeptides can be used to screen and isolate Mch4 or Mch5 polypeptides.

In addition, recombinant DNA methods currently used by those skilled in the art include the polymerase chain reaction (PCR) which, combined with the Mch4 or Mch5 nucleotide and amino acid sequence described herein, allows reproduction of Mch4 or Mch5 encoding sequences. Desired sequences can be amplified exponentially starting from as little as a single gene copy by means of PCR. The PCR technology is the subject matter of U.S. Pat. Nos. 4,683,195, 4,800,159, 4,754,065, and 4,683,202 all of which are incorporated by reference herein.

The above described methods are known to those skilled in the art and are described, for example, in Sambrook et al., *Molecular Cloning: A Laboratory Manual,* Cold Spring Harbor Laboratory, New York (1992) and the various references cited therein and in Ansubel et al., *Current Protocols in Molecular Biology,* John Wiley and Sons, Baltimore, Md. (1989); and in Harlow et al., *Antibodies: A Laboratory Manual,* Cold Spring Harbor, N.Y. (1989). These references and the publications cited therein are hereby expressly incorporated herein by reference.

The invention provides an isolated Mch4 or Mch5 polypeptides comprising substantially the amino acid sequence as that shown in FIGS. 1 and 2 (SEQ ID NOS:2 and 4). Mch4 or Mch5 functional fragments are also provided. Specific examples of Mch4 or Mch5 functional fragment are, for example, the catalytic domain which contain the active site amino acid sequence QACQC (SEQ ID NO:10) and the FADD-like domains Mch4A, Mch4B, Mch5A or Mch5B. When compared to the active site amino acid sequence of other ASCP family members, (SEQ ID NO:11) this active site sequence is similar but differs at position 4 with R substituted by Q.

Isolated Mch4 or Mch5 polypeptides of the invention can be obtained by a variety of methods known within the art. For example, the isolated peptides can be purified by biochemical methods including, for example, affinity chromatography. Affinity matrices which can be used for Mch4 or Mch5 isolation can be anti-Mch4 or anti-Mch5 monoclonal or polyclonal antibodies prepared against the sequence shown in FIGS. 1 and 2 (SEQ ID NOS:2 and 4), or fragments thereof such as synthetic peptides. Additionally, FADD-like domain binding polypeptides which are capable of binding the FADD-like domains at the N-terminus of Mch4 or Mch5 can also be used as affinity matrices. Alternatively, substrate analogues or enzymatic inhibitors of Mch4 or Mch5 can similarly be used as affinity matrices to isolate substantially pure Mch4 or Mch5 polypeptides of the invention.

Mch4 or Mch5 polypeptides can also be produced by recombinant methods known to those skilled in the art. Recombinant Mch4 or Mch5 polypeptides include, for example, an amino acid sequence substantially the same as that shown in FIGS. 1 and 2 (SEQ ID NOS:2 and 4) as well as fusion proteins and fragments thereof. The Mch4 or Mch5 encoding nucleic acids can be cloned into the appropriate vectors for propagation, manipulation and expression. Such vectors are known or can be construed by those skilled in the art and should contain all expression elements necessary for the transcription, translation, regulation, and if desired, sorting of the Mch4 or Mch5 polypeptides. The vectors can also be for use in either procaryotic or eucaryotic host systems so long as the expression and regulatory elements are of compatible origin. One of ordinary skill in the art will know which host systems are compatible with a particular vector. The recombinant polypeptides produced can be isolated by the methods described above.

Apoptosis plays a significant role in numerous pathological conditions in that programmed cell death is either inhibited, resulting in increased cell survival, or enhanced which results in the loss of cell viability. Examples of pathological conditions resulting from increased cell survival include cancers such as lymphomas, carcinomas and hormone dependent tumors. Such hormone dependent tumors include, for example, breast, prostate and ovarian cancer. Autoimmune diseases such as systemic lupus erythematosus and immune-mediated glomerulonephritis as viral infections such as herpesvirus, poxyvirus and adenovirus also result from increased cell survival or the inhibition of apoptosis.

In contrast, apoptotic diseases where enhanced programmed cell death is a prevalent cause generally includes, for example, degenerative disorders such as Alzheimer's disease, Parkinson's disease, Amyotrophic lateral sclerosis, Retinitis pigmentosa, and Cerebellar degeneration. Other diseases associated with increased apoptosis include, for example, myelodysplastic syndromes such as aplastic anemia and ischemic injury including myocaridal infarction, stroke and reperfusion injury.

The Mch4 or Mch5 encoding nucleic acids and polypeptides of the invention can be used to diagnose, treat or reduce the severity of cell death mediated diseases such as those described above as well as other diseases mediated by either increased or decreased programmed cell death. Additionally, the Mch4 or Mch5 encoding nucleic acids and polypeptides of the invention can be used to screen for pharmaceutical compounds and macromolecules which inhibit or promote Mch4 or Mch5 mediated apoptosis.

For example, the Mch4 or Mch5 encoding nucleic acids, polypeptides and functional fragments thereof can be used to diagnose, or to generate reagents to diagnose diseases mediated or characterized by programmed cell death. Diagnosis can be by nucleic acid probe hybridization with Mch4 or Mch5 containing nucleotide sequences, antibody or ligand mediated detection with Mch4 or Mch5 binding agents or by enzyme catalysis of detectable Mch4 or Mch5 substrates. Such methods are routine to those skilled in the art. Detection can be performed ex vivo, for example, by removing a cell or tissue sample from an individual exhibiting or suspected of exhibiting a cell death mediated disease. Correlation of increased Mch4 or Mch5 expression or activity is indicative of diseases characterized by enhanced programmed cell death whereas correlation of decreased Mch4 or Mch5 expression or activity is indicative of diseases characterized by the inhibition of programmed cell death.

The above Mch4 or Mch5 polypeptides can also be formulated into pharmaceutical compositions known within the art for the treatment of cell death mediated diseases characterized by increased cell survival and proliferation. Functional fragments and peptides such as the FADD-like domains and the catalytic domain of Mch4 or Mch5 can similarly be formulated for the treatment of such diseases associated with increased cell survival and proliferation. Additionally, molecules which interact with Mch4 and Mch5 can additionally be used to induce Mch4 and Mch5 mediated apoptosis. Such molecules can include, for example, FADD and FADD or fasactivators. Administration of Mch4 or Mch5 polypeptides and functional fragments thereof will induce apoptosis in treated cells and eliminate those cells characterized by increased cell survival or proliferation. Administration of non-Mch4 or Mch5 polypeptides that do not directly act on Mch4 or Mch5 substrates but induce the activation of the Mch4 or Mch5 protease can similarly be used for the treatment of diseases characterized by increased cell survival and proliferation.

To be effective, the Mch4 or Mch5 polypeptides must be introduced into the cells characterized by increased cell survival. Introduction can be accomplished by a variety of means known within the art including, for example, lipid vesicles and receptor mediated endocytosis. Targeting to the appropriate cell type can similarly be accomplished through conjugation to specific receptor ligands, specific target cell antibodies and the like.

The Mch4 or Mch5 polypeptides are administered by conventional methods, in dosages which are sufficient to induce apoptosis in the cells characterized by increased cell survival or proliferation. Such dosages are known or can be easily determined by those skilled in the art. Administration can be accomplished by, for example, intravenous, interperitonal or subcutaneous injection. Administration can be performed in a variety of different regimes which include single high dose administration or repeated small dose administration or a combination of both. The dosing will depend on the cell type, progression of the disease and overall health of the individual and will be known or can be determined by those skilled in the art.

In contrast to the induction of Mch4 or Mch5 mediated apoptosis for the treatment of pathological conditions characterized by increased cell survival or proliferation, inhibitors of Mch4 or Mch5 can be used to treat diseases characterized by increased programmed cell death. Such inhibitors can be, for example, inhibitors of the Mch4 or Mch5 protease activity or inhibitors of the conversion of the inactive, pro-Mch4 or pro-Mch5 into the active Mch4 and Mch5 proteases, or alternatively inhibitors of the binding activity of the FADD-like domains. Specific examples of such inhibitors can include, for example, anti-Mch4 or anti-Mch5 antibodies, proteins, or small peptidyl protease inhibitors, or small non-peptide, organic molecule inhibitors which are formulated in a medium which allows introduction into the desired cell type. Alternatively, such inhibitors can be attached to targeting ligands for introduction by cell mediated endocytosis and other receptor mediated events. Specific examples of Mch4 or Mch5 peptidyl inhibitors are described in Table I of Example III and includes suicide inhibitors and substrate analogues such as the tetrapeptide (SEQ ID NO:71) and the cowpox virus protein Crm A, for example.

Other inhibitors of Mch4 or Mch5 include, for example, small molecules and organic compounds which bind and inactivate Mch4 or Mch5 by a competitive or non-competitive type mechanism. Molecules or compounds which indirectly inhibit the Mch4 or Mch5 pathway can also be used as inhibitors of Mch4. Mch4 or Mch5 inhibitors can be identified by screening for molecules which demonstrate specific or beneficial Mch4 or Mch5 inhibitory activity. Such methods are described further below and can be practiced by those skilled in the art given the Mch4 or Mch5 nucleotide and amino acid sequences described herein.

Dominant/negative inhibitors of Mch4 or Mch5 can also be used to treat or reduce the severity of diseases characterized by increased programmed cell death. In this regard, Mch4 or Mch5 large subunits which lack the active site (SEQ ID NO:10) can be used to bind the small subunits of Mch4 or Mch5 and prevent active protease complexes from forming. Such a mechanism of dominant negative inhibition of Mch4 is similar to the dominant negative inhibition of Ich-$1_L$ by Ich-$1_S$. Subunits from other ASCPs can similarly be used as dominant/negative inhibitors of Mch4 or Mch5 activity and therefore treat diseases mediated by programmed cell death. Such subunits should be selected so that they bind either the p17 or p12 Mch4 or Mch5 polypeptides and prevent their assembly into active tetrameric protease complexes. Moreover, Mch4 or Mch5 subunits which have been modified so as to be catalytically inactive can also be used as dominant negative inhibitors of Mch4. Such modifications include, for example, mutation of the active site cysteine residue to include but not limited to Alanine or glycine.

Mch4 or Mch5 substrate antagonists can similarly be used to treat or reduce the severity of diseases mediated by increased programmed cell death. Such substrate antagonists can bind to and inhibit cleavage by Mch4. Inhibition of substrate cleavage prevents commitment progression of programmed cell death. Substrate antagonists include, for example, ligands and small molecule compounds.

Treatment or reduction of the severity of cell death mediated diseases can also be accomplished by introducing expressible nucleic acids encoding Mch4 or Mch5 polypeptides or functional fragments thereof into cells characterized by such diseases. For example, elevated synthesis rates of Mch4 or Mch5 can be achieved by, for example, using recombinant expression vectors and gene transfer technology. Similarly, treatment or reduction of the severity of cell death mediated diseases can also be accomplished by introducing and expressing antisense Mch4 or Mch5 nucleic acids so as to inhibit the synthesis rates of Mch4 or Mch5. Such methods are well known within the art and will be described below with reference to recombinant viral vectors.

Other vectors compatible with the appropriate targeted cell can accomplish the same goal and therefore can be substituted in the methods described herein in place of recombinant viral vectors.

Recombinant viral vectors are useful for in vivo expression of a desired nucleic acid because they offer advantages such as lateral infection and targeting specificity. Lateral infection is inherent in the lifecycle of retroviruses and is the process by which a single infected cell produces many progeny virions that bud off and infect neighboring cells. The result is a large area becomes rapidly infected, most of which were not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Typically, viruses infect and propagate in specific cell types. Therefore, the targeting specificity of viral vectors utilizes this natural specificity to in turn specifically introduce a desired gene into predetermined cell types. The vector to be used in the methods of the invention will depend on desired cell type to be targeted. For example, if neurodegenerative diseases are to be treated by decreasing the Mch4 or Mch5 activity of affected neuronal cells then a vector specific for cells of the neuronal cell lineage should be used. Likewise, if diseases or pathological conditions of the hematopoietic system are to be treated, than a viral vector that is specific for blood cells and their precursors, preferably for the specific type of hematopoietic cell, should be used. Moreover, such vectors can additionally be modified with specific receptors or ligands and the like to modify or alter target specificity through receptor mediated events. These modification procedures can be performed by, for example, recombinant DNA techniques or synthetic chemistry procedures. The specific type of vector will depend upon the intended application. The actual vectors are also known and readily available within the art or can be constructed by one skilled in the art using well known methodology.

Viral vectors encoding Mch4 or Mch5 nucleic acids or inhibitors of Mch4 or Mch5 such as antisense nucleic acids can be administered in several ways to obtain expression of such sequences and therefore either increase or decrease the activity of Mch4 or Mch5 in the cells affected by the disease or pathological condition. If viral vectors are used, for example, the procedure can take advantage of their target specificity and consequently, do not have to be administered locally at the diseased site. However, local administration can provide a quicker and more effective treatment. Administration can also be performed by, for example, intravenous or subcutaneous injection into the subject. Injection of the viral vectors into the spinal fluid can also be used as a mode of administration, especially in the case of neurodegenerative diseases. Following injection, the viral vectors will circulate until they recognize host cells with the appropriate target specificity for infection.

As described above, one mode of administration of Mch4 or Mch5 encoding vectors can be by direct inoculation locally at the site of the disease or pathological condition. Local administration is advantageous because there is no dilution effect and therefore a smaller dose is required to achieve Mch4 or Mch5 expression in a majority of the targeted cells. Additionally, local inoculation can alleviate the targeting requirement required with other forms of administration since a vector can be used that infects all cells in the inoculated area. If expression is desired in only a specific subset of cells within the inoculated area then promoter and expression elements that are specific for the desired subset can be used to accomplish this goal. Such non-targeting vectors can be, for example, viral vectors, viral genomes, plasmids, phagemids and the like. Transfection vehicles such as liposomes can be used to introduce the non-viral vectors described above into recipient cells within the inoculated area. Such transfection vehicles are known by one skilled within the art. Alternatively, however, nontargeting vectors can be administered directly into a tissue of any individual. Such methods are known within the art and are described by, for example, Wolff et al. (*Science* 247:1465–1468 (1990)).

Additional features can be added to the vectors to ensure safety and/or enhance therapeutic efficacy. Such features include, for example, markers that can be used to negatively select against cells infected with the ) recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce mutant forms of Mch4 or Mch5, dysfunction of apoptosis will not occur.

As described previously, the Mch4 or Mch5 encoding nucleic acids and Mch4 or Mch5 polypeptides of the invention can be used to screen for compounds which inhibit or enhance the expression of Mch4 or Mch5 mediated apoptotic activity. Mch4 or Mch5 mediated apoptotic activity includes, for example, both the protease activity of these ASCPs and/or the FADD-like domain binding activity. Such screening methods are known to those skilled in the art and can be performed by either in vitro or in vivo procedures. For example, described in Example II is a specific in vitro assay for Mch4 or Mch5 protease activity. This assay employs Mch4 or Mch5 polypeptide expressed in an active, processed form recombinantly in *E. coli,* whose protease activity is measured by incubation with a fluorescent substrate (SEQ ID NO:71). Also described therein are peptide and polypeptide inhibitors of Mch4. This assay can be used to screen synthetic or naturally occurring compound libraries, including macromolecules, for agents which either inhibit or enhance Mch4 or Mch5 activity. The Mch4 or Mch5 polypeptides to be used in the assay can be obtained by, for example, in vitro translation, recombinant expression or biochemical procedures. Methods other than that described in Example II can also be used to screen and identify compounds which inhibit Mch4 or Mch5. Such methods can include, for example, binding assays such as ELISA and RIAs using FADD-like domain binding proteins. A specific example is phage display peptide libraries where greater than $10^8$ peptide sequences can be screened in a single round of panning. Such methods as well as others are known within the art and can be utilized to identify compounds which inhibit or enhance Mch4 or Mch5 activity.

It is understood that modifications which do not substantially affect the activity of the various embodiments of this invention are also included within the definition of the invention provided herein. Accordingly, the following examples are intended to illustrate but not limit the present invention.

EXAMPLE I

Cloning and Characterization of Mch4

This Example shows the cloning, sequence analysis and tissue distribution of Mch4 and Mch5. The results described herein indicate that Mch4 and Mch5 are novel members of the cell death family of aspartate-specific cysteine proteases.

To identify potentially novel members of the ICE family of cysteine proteases, an approach combining information from the GenBank database of human expressed sequence tags (ESTs) and PCR was employed. Initially, Ced-3/ICE-like apoptotic cysteine proteases from Jurkat T-lymphocytes were enriched by amplification of a human Jurkat cDNA library using degenerate PCR primers encoding the conserved GSWFI/GSWYI SEQ ID NO:69 and 70 respectively pentapeptides (Femandes-Alnermi et al., Cancer Res. 55:2737–2742 (1995a)). This amino acid sequence has been found to be conserved among ICE family members. Briefly, a 10 μl aliquot of human Jurkat λ Uni-Zap™ XR cDNA library containing approximately $10^8$ pfu was denatured at 99° C. for 5 min. and used as a substrate for PCR amplification with a degenerate primer encoding the pentapeptide GSWFI/GSWYI (SEQ ID NO:69 and 70 respectively) and a T3 vector-specific primer (Stratagene).

The enriched library was then amplified with a primer derived from an EST sequence identified in a homology search of the GenBank database using a query nucleotide sequence corresponding to the Mch2 and CPP32 coding sequence. The secondary amplification was performed starting with a 10 μl aliquot of the above amplified sequences combined with a primer derived from the GenBank sequence T96912 (primer T96-prl: TCAGCCTCGGCAG-GAATAC SEQ ID NO:5) and a second vector specific primer (SK-Zap: CAGGAATTCGGCACGAG, SEQ ID NO:6). The secondary amplification products were cloned into a Sma I cut pBluescript II KS+vector. All clones were screened by PCR using a degenerate oligonucleotide corresponding to the conserved active site amino acid sequence QACRG (SEQ ID NO:11) and the SK-Zap primer. Clones that were positive for the presence of the QACRG (SEQ ID NO:11) coding sequence were then subjected to DNA sequencing using T3 and T7 sequencing primers (Stratagene). This amplification and screen resulted in the identification of a Ced-3/ICE-like partial cDNA with high homology to CPP32 and Ced-3.

Partial cDNA identified from the (SEQ ID NO:11) screening was then excised from the vector, radiolabeled and used to screen the original Jurkat λ Uni-Zap™ XR cDNA library for full length cDNA clones. Positive λ clones were purified, rescued into the pBluescript II SK⁻ plasmid vector and sequenced.

The above screening identified a 3.6 kb cDNA clone from the human Jurkat T-lymphocyte CDNA library. This cDNA contains an open reading frame of 1437 bp that encodes a 479-amino acid protein, named Mch4 (SEQ ID NOS:1 and 2, respectively). As shown in FIGS. 1 and 3A, proMch 4 is a polypeptide of 479 amino acid residues with a predicted molecular mass of 55 kDa. Although discussed more fully below in regard to the tissue distribution, the Mch4 polypeptide is encoded by an approximately 4.0 kb MRNA. This size, together with the presence of an in-frame stop codon 12 bp upstream from the initiator methionine indicates that the cloned Mch4 cDNA (SEQ ID NO:1) contains the full length coding region.

Following identification of and cloning of Mch4, a subsequent search of the GenBank database resulted in the identification of a second novel EST sequence (N42544) with extensive homology to Mch4. Briefly, a homology search of the GenBank database of human expressed sequence tags (ESTS) for sequences similar to Mch4 revealed a 449 bp EST sequence (N42544) with a 64% identity to Mch4. Using PCR primers derived from that EST sequence (Mch5-prl, GACAGAGCGAGATTCTGT; Mch5-pr2, GCACCATCAATCAGAAGG (SEQ ID NOS:7 and 8, respectfully)) and the vector specific primers T3 and SK-Zap, the full length cDNA corresponding to this gene was amplified by PCR from the Jurkat cDNA library and cloned in KS-vector. To perform this amplification, the Mch5-prl and the T3 vector primers were used for the primary PCR amplification step to amplify 5' sequences of Mch5 while the Mch5-pr2 and the SK-Zap vector specific primer was used for the secondary amplification step. The full length cDNA was sequenced and its gene product was named Mch5 (SEQ ID NO:3).

The Mch5 cDNA encodes an about 496 amino acid protein (SEQ ID NO:4) with the highest degree of homology to Mch4 compared to other family members. Excluding the prodomain, the overall sequence identity between Mch4 and Mch5 is about 46%. A comparison of the amino acid sequence identities between FADD and the FADD-like domain within Mch4 and Mch5 is shown in FIG. 3A while a multiple amino acid sequence aligmnent of all known ASCPs is shown in FIG. 3B. Although the sequence comparisons of Mch4 and Mch5 are discussed further below. These results indicate that Mch4 and Mch5 are in fact distinct ASCPs and not variants of a single gene product.

The identification and sequence analysis of the novel apoptotic proteases described herein has now revealed that both Mch4 and Mch5 belong to the Ced-3-like subfamily of ASCPs. Briefly, previously identified ASCPs can be divided phylogenetically into three subfamilies. The Ced-3-like ASCP subfamily includes Ced- 3, (SEQ ID NOS:37–41) CPP32, (SEQ ID NOS:32–36) Mch2, and Mch3 SEQ ID NOS:22–26. The ICE-like ASCP subfamily includes ICE (SEQ ID NOS:27–31), TX (SEQ ID NOS:42–46) (ICH2, ICErel-II, Mih1) and ICErelIII SEQ ID NOS:52–56. The NEDD-like subfamily include ICH-1 and its mouse counterpart NEDD2 (SEQ ID NO:16). Sequence alignment of Mch4 and Mch5 with these known ASCPs is shown in FIG. 3B and reveals both of these new ASCPs belong to the Ced-3-like subfamily of ASCPs.

Both Mch4 and Mch5 contain N-terminal FADD-like death effector domains. The N-terminal death effector domain of FADD (Hsu et al., Cell, 84:299–308 (1996)) can bind one of the two FADD-like domains in either Mch4 or Mch5 for activation and recruitment to Fas-apoptotic pathway. Activation of Mch4 or Mch5 by FADD can, for example, lead to activation of downstream proteases such as CPP32 and Mch3. Shown in FIG. 3A is multiple amino acid sequence alignment of FADD and each of the FADD-like domains within Mch4 (Mch4A and Mch4B) and within Mch5 (Mch5A and Mch5B).

Shown in FIG. 3B is a multiple amino acid sequence alignment of relatively conserved regions within the ASCPs. These regions include, for example, (1) the active site pentapeptide QACRG (SEQ ID NO:11), (2) the substrate binding residues P1–P4 and (3) the putative processing sites between the small and large subunits. Relevant sequence comparisons for each of these regions as well as other worthy distinctions is discussed more fully below.

For example, in the region that does not contain the propeptide domain, Mch4 and Mch5 are equally related to Ced-3 (SEQ ID NO:9) exhibiting an overall amino acid identity of 32% and sequence similarity of 54%. Comparing with the other human Ced-3-like subfamily members, Mch4 is more related to Mch2 and Mch3 (SEQ ID NO:11 and 12, respectfully) with a 38–40% sequence identity and a 56–58% similarity than it is to CPP32 (SEQ ID NOS:32–36). The latter comparison revealing a 35% amino acid identity and a 57% amino acid sequence similarity. On the other hand, Mch5 is equally related to CPP32, Mch2 and Mch3 with a 39–40% amino acid sequence identity and a 60–62% sequence similarity.

Comparison of Mch4 and Mch5 reveals a significant degree of homology with an overall sequence identity of 52% and similarity of 67% at the primary amino acid level excluding the propeptide domain. As shown in FIG. 3B, the homology between the two proteins is highest within the small subunit region. A similar relationship was observed with other family members such as CPP32/Mch3 and ICE/TX. These sequence similarities indicate that Mch4 and Mch5 similarly likely interact with each other as do their related family members CPP32 and Mch3 (Femandes-Alnemri et al., Cancer Res. 55:6045–6052 (1995b)). For example, Mch4 and Mch5 likely heterodimerize with each other to form functional protease heterocomplexes as do CPP32 and Mch3.

Sequence alignment also revealed that, although distinct, Mch4 and Mch5 are structurally similar to other known ASCPs. The active enzymes of Mch4 and Mch5 are made of two subunits, derived from precursor proenzymes (Mch4 and Mch5) by cleavage at highly conserved Asp residues (Asp239 in Mch4 and Asp284 in Mch5) located between the two subunits (denoted as D/X in FIG. 3B) Consistent with other ASCPs, Mch4 and Mch5 are likely processed further to remove the propeptide domains. Several aspartate cleavage sites are present in the prodomain region of both Mch4 and Mch5 (FIG. 3A).

Regardless of the above similarities, one major difference between Mch4 and Mch5 and other family members is that their active site pentapeptide contains an Arg to Gln non-conservative substitution. The substitution changes the previously conserved peptapeptide sequence from QACRG (SEQ ID NO:11) to QACQG SEQ ID NO:10. Such a substitution could have major effects on enzyme and substrate specificities. The presence of QACQG SEQ ID NO:10 instead of QACRG in these two enzymes, suggests that other unknown family members with a similar substitution may exist. This result further increases the complexity of the ASCP family.

Another major difference between Mch4 and Mch5 and other ASCP family members is the inclusion of multiple FADD-like domains at their amino termini. The inclusion of these domains indicates that they can interact with FADD early within the fas mediated apoptotic pathway to regulate programmed cell death. Consequently, FADD may bind the FADD-like domains in Mch4 or Mch5 for activation and recruitment to the fas apoptotic pathway. This recruitment occurs because FADD-like domains are capable of both homotypic and heterotypic interactions (Bold et al., J. Biol. Chem. 270:7795–7798 (1995); Chinnaiyan et al., Cell 81:505–512 (1995); Hsu et al., supra, 1996).

In regard to specific amino acid residues that have been implicated to play functional roles, the crystal structure of ICE has indicated that the amino acid residues His237, Gly238 and Cys285 are involved in catalysis, while Arg179, Gln283, Arg341 and Ser347 are involved in binding the carboxylate side chain of the substrate P1 aspartate. With the exception of Ser347 in Mch5, all of these other residues are absolutely conserved in all family members. Nevertheless, the Ser to Thr substitution in Mch5 corresponding to Ser347, is a conservative substitution and it is the only one among all the family members (FIG. 3B). Another Ser to Thr conservative substitution can also be seen in Mch4 in the region corresponding to Ser236. This residue is one that participates in binding the substrate P2-P4 residues. However, others residues that might participate in binding the substrate P2-P4 residues are not widely conserved. This result indicates that these other residues likely determine substrate specificity.

EXAMPLE II

Tissue Distribution and Chromosomal Localization of Mch4

This Example shows the expression pattern of Mch4 as measured by RNA blot analysis and the genetic locus of the Mch4 gene.

The tissue distribution of Mch4 was analyzed by RNA blot analysis of poly A$^+$RNA isolated from different human tissues. Briefly, tissue distribution analysis of Mch4 MRNA was performed on RNA blots prepared by Clontech (San Diego, Calif.) containing 2 µg/lane of poly A$^+$RNA from each tissue of origin. A radioactive Mch4 riboprobe was prepared using Mch4 cDNA as a template for T7 RNA polymerase in the presence of [$\alpha^{32}$P]ATP. The blots were hybridized, washed and then visualized by autoradiography.

The results of the RNA blots revealed that a major 3.7 Kb Mch4 message was detectable in most tissues examined. The lowest expression of Mch4 mRNA was seen in whole brain, kidney, prostate, testis and colon. The size of the Mch4 MRNA is consistent with the length of the cloned Mch4 cDNA (3.6 kb). Other higher molecular weight mRNA species can also be seen in some tissues such as skeletal muscle, for example, and could represent unprocessed Mch4 MRNA or an mRNA of a related family member.

To determine the chromosomal localization of the Mch4 gene, a panel of rodent-human somatic cell hybrids was screened by PCR with Mch4 specific primers. Briefly, A panel of DNAs from rodent-human somatic cell hybrids was screened by PCR with the previously described Mch4 specific primers t96-prl (SEQ ID NO:5) and a second Mch4 specific primer termed t96-pr5 (CGGGAGATCATGTCTCAC, SEQ ID NO:9. These primers were also used to screen by PCR the CEPH A and B YAC libraries.

The results of these searches identified two YAC clones (756A9 and 800G4) which were positive for Mch4. A computer search through the Whitehead Institute and CEPH databases showed that both YACS were part of the WI contigs WC-630 and Wc2.16 and of the CEPH contig at position 2.08 of chromosome 2. Other YACS (741D10, 762C12, 809H8, and 828E8) reported by the databases to overlap with 756A9 and/or 800G4 were tested by PCR for the presence of Mch4 gene sequences. Clones 762C12 and 828E8 were found to be positive for Mch4. This analysis resulted in the assignment of Mch4 to chromosome 2pl2-qter. To confirm these mapping results and to obtain a definite physical localization for the Mch4 gene, the non-chimeric YAC 828E8 was used in FISH analysis to probe normal human lymphocyte metaphases. The Mch4 chromosomal localization was narrowed to chromosome 2q33-34 using this latter analysis. This places the Mch4 gene within a 4cM region flanked by the centromeric marker D2S374 and the telomeric marker D2S346 (Chumakov et al., Nature 377(supp.):175–183 (1995)).

EXAMPLE III

Kinetic Parameters of Mch4

This Example characterizes the protease activity and substrate specificity of the ASCP Mch4.

The kinetic properties of bacterially expressed recombinant Mch4 were determined using the tetrapeptide substrates DEVD-AMC and YVAD-AMC in a continuous fluorometric assay (Table I). The DEVD-AMC and the YVAD-AMC represent the cleavage sites for the poly(ADP-ribose) polymerase (PARP) and IL-1β P1–P4 substrate tetrapeptides, respectively (Nicholson et al., Nature 376:37–43 (1995)). Briefly, Mch4 cDNA lacking most of the propeptide coding sequence (amino acids 61–346) was subcloned in-frame into the Bam HI/AhoI sites of the bacterial expression vector pGEX-5X-3 (Pharmacia Biotech Inc.). This vector produces Mch4 as a fusion protein with glutathione S-transferase (GST) and was used essentially as described in Femades-Alnemri et al., supra (1995a). The GST-Mch4 expression vector was constructed and transformed into DH5α bacteria using routine molecular biology methods known to those skilled in the art. After induction with IPTG, bacterial extracts were prepared from E. coli expressing the recombinant fusion proteins. The extracts were adsorbed to glutathione-Sepharose resin, washed several times and then analyzed by SDS-PAGE. The Mch4 preparation contained a protein that migrated as a doublet of approximately 50 kDa (GST-large subunit fusion) and 12 kDa (small subunit).

The purified Mch4 GST-fusion protein was then used for further enzymatic analyses. The activity of Mch4 was measured using bacterial lysates prepared with ICE buffer (25 mM HEPES, 1 mM EDTA, 5mM DTT, 0.1% CHAPS, 10% sucrose, pH 7.5) at room temperature (24–25° C.). The Ki's were determined from the hydrolysis rate of 50 μM DEVD-AMC following a 30 min preincubation of the enzyme with inhibitors DEVD-CHO and recombinant CrmA protein. Prior to incubation with enzyme, purified CnnA was activated by incubation with 5 mM DTT for 10 min at 37° C.

TABLE I

Kinetic Parameters of Mch4

| Parameter | Value |
|---|---|
| $K_m$(DEVD-AMC) | 130 μM |
| $K_m$(YVAD-AMC) | 150 μM |
| $K_i$(DEVD-CHO) | 14 nM |
| $K_i$(CrmA) | 0.75 μM |

As shown above in Table I, the $K_m$ values of Mch4 for the two peptide substrates DEVD-AMC and YVAD-AMC are similar. These values contrast with those for CPP32, where the $K_M$ for the YVAD-AMC substrate is >35-fold higher than the $K_M$ for the DEVD-AMC substrate (Femandes-Alnemri et al. supra (1995b)). These kinetic references are further illustrated by the ratio of Vmax/Km for the DEVD-AMC substrate. Specifically, CPP32 possesses a >500-fold higher specificity for this substrate compared to Mch4 ($V_{max}K_{MCPP32}$=9200 and $V_{max}/K_{Mch4}$=18). However, similar to CPP32 and Mch3a, Mch4 is potently inhibited by the DEVD-CHO peptide $K_{iMch4}$=14 nM) and weekly inhibited by Cnn A ($K_{iMCh4}$=0.75 μM) (Femandes-Alnemri et al., supra (1995b)). Since DEVD-CHO also blocks cell death, this result further indicates that Mch4 is an ASCP which plays a role in the cell death pathway.

EXAMPLE IV

Granzyme B Activates Multiple Members of the Mammalian Ced-3 Subfamily

This Example shows that the cytotoxic T cell protease essential for induction of apoptosis in target cells directly activates ASCP members of the Ced-3 subfamily by cleavage into the large and small protease subunits.

Granzyme B has been shown to cleave CPP32 to generate an ~20 kDa cleavage product presumed to be the large subunit of CPP32 (Darnon et al., Nature 377:446–448 (1995)). This cleavage event has attracted the idea that the granzyme B cleavage occurs at the processing sequence IETD-S between the two subunits of CPP32 (FIG. 3B). Sequence comparison of the Mch4 and Mch5 ASCPs described herein has revealed that the potential processing sequences between the two subunits of Mch3 and Mch4 are very similar to that of CPP32 (FIG. 3B). These two sequences contain identical P1 residues (CPP32-D175, Mch3-D198, Mch4-D239) and P4 residues (CPP32-I172, Mch3-I195, Mch4-I236) in all three proenzymes and a conserved P3 residue (CPP32-E173, Mch3-Q197, Mch4-E237), suggesting that if the processing site in CPP32 is in fact cleaved by granzyme B, then these other subfamily members may similarly be substrates for cleavage as well.

To determine whether granzyme B can cleave these proenzymes at the proposed processing sites, mutant proenzymes with a P1 substitution mutation converting D to A in CPP32 and Mch3 or a D to G in Mch4 were generated. Briefly, potential aspartate processing sites between the two subunits of these ASCPs were mutated to alanine (CPP32 and Mch3) or glycine (Mch4) by site directed mutagenesis using overlapping PCR mutagenic oligonucleotides. Two internal mutagenic overlapping oligonucleotide primers encoding the D/A or the DIG mutation and two external oligonucleotides encoding the first six N-terminal amino acids and last six C-terminal amino acids, respectively, were used in a PCR reaction with CPP32, Mch3 and Mch4 cDNAs. Asp9 of proCPP32 was mutated to Ala by PCR using a 5' mutagenic oligonucleotide encoding the D to A mutation and a 3'- primer derived from the 3'-noncoding sequence of CPP32 cDNA. The resulting PCR products were subcloned in pBluscript II $KS^+$ vector under the T7 promoter and their sequence was verified by DNA sequencing.

Wild type and mutated cDNAs were in vitro transcribed and translated in the presence of $^{35}$S-methionine using Promega coupled transcription/translation TNT kit according to the manufacturer recommendations. Two microliters of the translation reactions were incubated with purified enzymes (100–200 ng) or bacterial lysates expressing recombinant ASCPs in ICE-buffer, in a final volume of 10 μl. The reaction was incubated at 37° C. for 1–2 hours and then analyzed by SDS-PAGE and autoradiography.

Figure 4A:
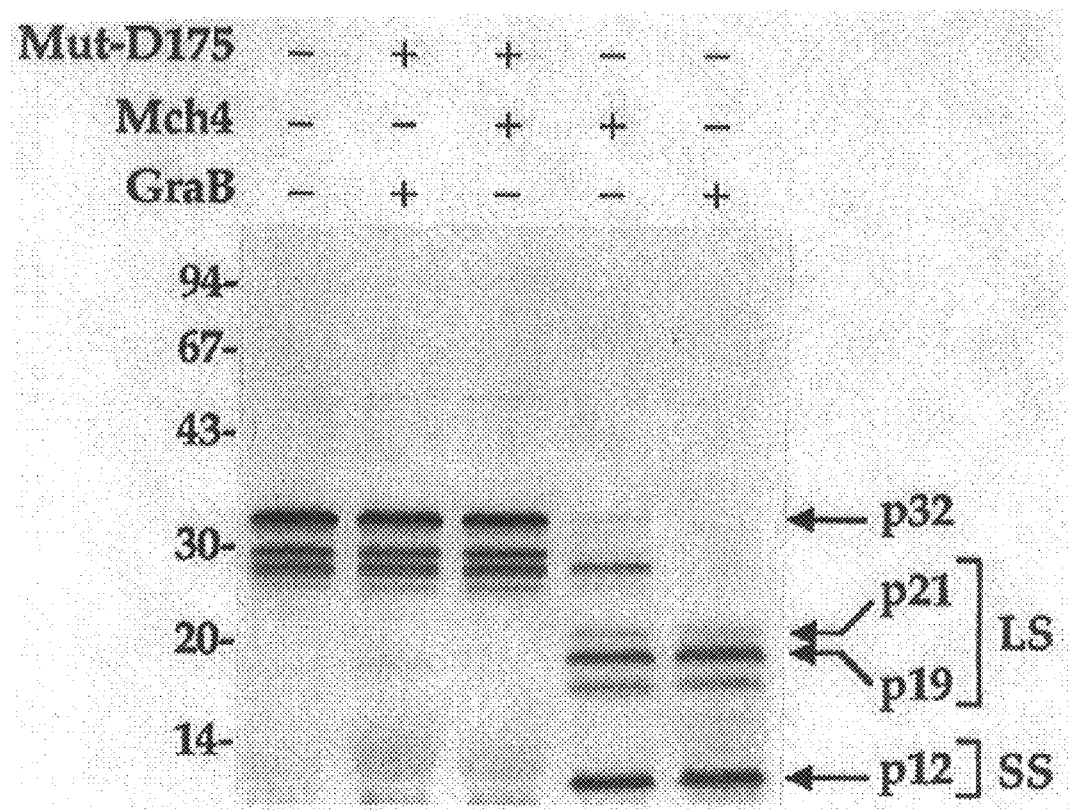
FIG. 4 shows the cleavage of CPP32 proenzyme by Mch4 and granzyme B. (A) Effect of Asp175 mutation on cleavage of proCPP32. $^{35}$S-labeled wild type proCPP32 (Mut-D175, −lanes) or Asp175-mutated proCPP32 (Mut-D175, +lanes) were incubated with recombinant Mch4 (Mch4, +lanes), granzyme B (GraB, +lanes) or buffer (Mch4 and GraB, −lanes) for 1 h at 37° C. The reaction products were then analyzed by SDS-PAGE and autoradiography. (B) Effect of Asp9 mutation and the DEVD-CHO inhibitor on cleavage of the propeptide of proCPP32. 35S-labeled wild type proCPP32 (mut-D9 and Mut-175, −lanes) or Asp9-mutated (mut-D9, +lanes) or Asp 175-mutated (Mut-D175, +lanes) proCPP32 were incubated with granzyme B (GraB, +lines) or buffer (GraB, −lanes) in the presence (+lanes) or absence (−lanes) of the DEVD-CHO inhibitor. The reaction products were analyzed as above. SS, indicates the small subunit. LS, indicates the large subunit.

Following in vitro translation, the parental and mutant proenzymes were incubated with granyme B and then analyzed by SDS-PAGE and autoradiography. As shown in FIG. 4A, in vitro translation of wild type (lane 1) or Asp175-mutated (lanes 2 and 3) CPP32 proenzymes generated identical pattern of translation products. The major translation products started with Met27 and Met39, respectively. Incubation of these translation products with granzyme B resulted in cleavage of the wild type proCPP32 at Asp175 (lane 5) to generate the two subunits of active CPP32. The small C-terminal subunit migrates as a single ~12 kDa band and the large N-terminal subunit migrates as three bands (~21, ~19 and ~17 kDa).

Figure 4B:
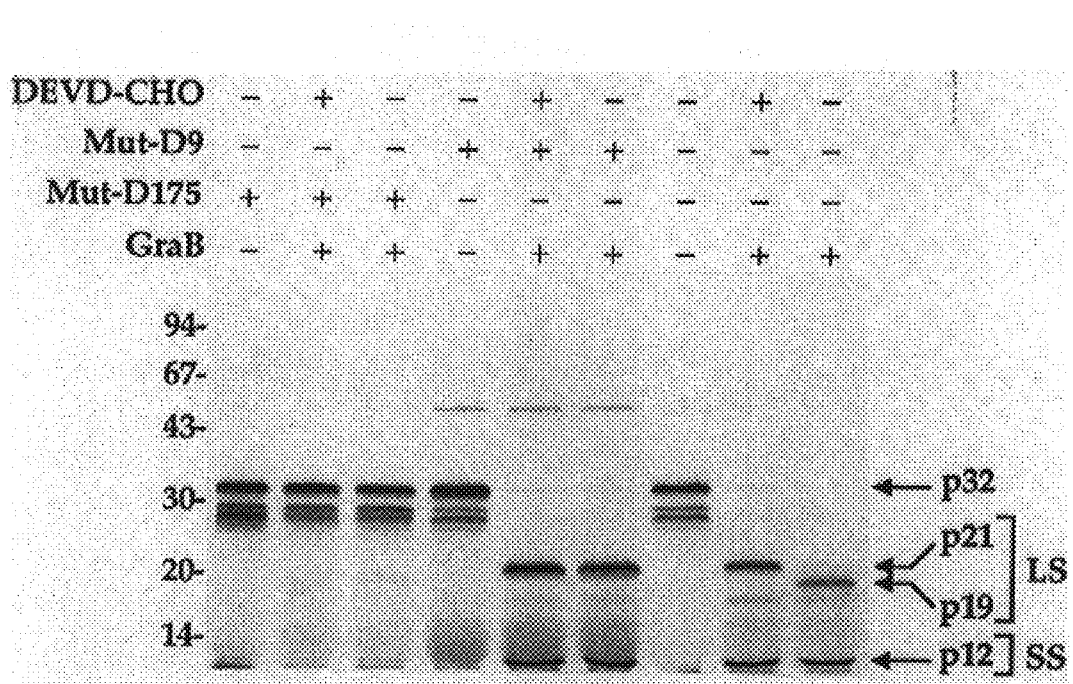

In regard to the identities of the bands comprising the large subunit, the faint ~21 kDa band is most likely a cleavage product of the full length proCPP32. However, the high intensity of the ~19 kDa band suggests that it is produced from the ~21 kDa band by further processing at the propeptide domain. This indication is supported by the observation that incubation of proCPP32 with granzyme B in the presence of the CPP32 peptide inhibitor DEVD-CHO, generated a major ~21 kDa band which was not further processed to the ~19 kDa band (FIG. 4B, lane 8). Further processing of the ~21 kDa band to the ~19 kDa band was only observed in the absence of the peptide inhibitor DEVD-CHO (FIG. 4A, lane 5 and FIG. 4B, lane 9). This result indicates that the additional processing of the propeptide domain seen with the wild type proCPP32 is due to the autocatalytic activity of the granzyme B-activated CPP32. No cleavage was observed with the buffer control or the Asp175-mutated CPP32 (FIG. 4A, lanes 1 and 3, respectively).

In addition there was no cleavage at the propeptide domain of the Asp175-mutated CPP32 (FIG. 4A, lane 2 and FIG. 4B, lane 3), indicating further support to our earlier conclusion that cleavage of the propeptide is an autocatalytic activity of activated CPP32. Furthermore, the autocatalytic processing within the propeptide domain occurs at Asp9 and not at Asp28. Mutation of Asp9 to Ala inhibited the processing of the ~21 kDa band to the ~19 kDa band in a similar fashion as observed with the DEVD-CHO inhibitor (FIG. 4B, lanes 5 and 6). These data indicate that CPP32 is autocatalytically processed at Asp9 after activation to generate a p19 (large subunit) and p12 (small subunit).

Earlier observation that purified human CPP32 was processed at Asp28, could be due to the fact that CPP32 was purified from THP-1 monocyte cytosol after incubation at 37° C. for several hours (Nicholson et al., supra (1995)). THP-1 cytosol contains high concentration of ICE and possibly other ICE homologs that might be responsible for the additional processing at Asp28. The ~17 kDa band is a cleavage product of one of the smaller internally translated products, most likely the 29 kDa band.

Similarly, in vitro translation of wild type or Asp198-mutated proMch3 (FIG. 5A, lanes 1 and 2, respectfully) generated two major products. These two translation products are a 35–36 kDa product corresponding to the full length proMch3 and a 30 kDa internal translation production most likely starting with Met45. Other internal translation products smaller than 30 kDa can also be seen.

Figure 5A:
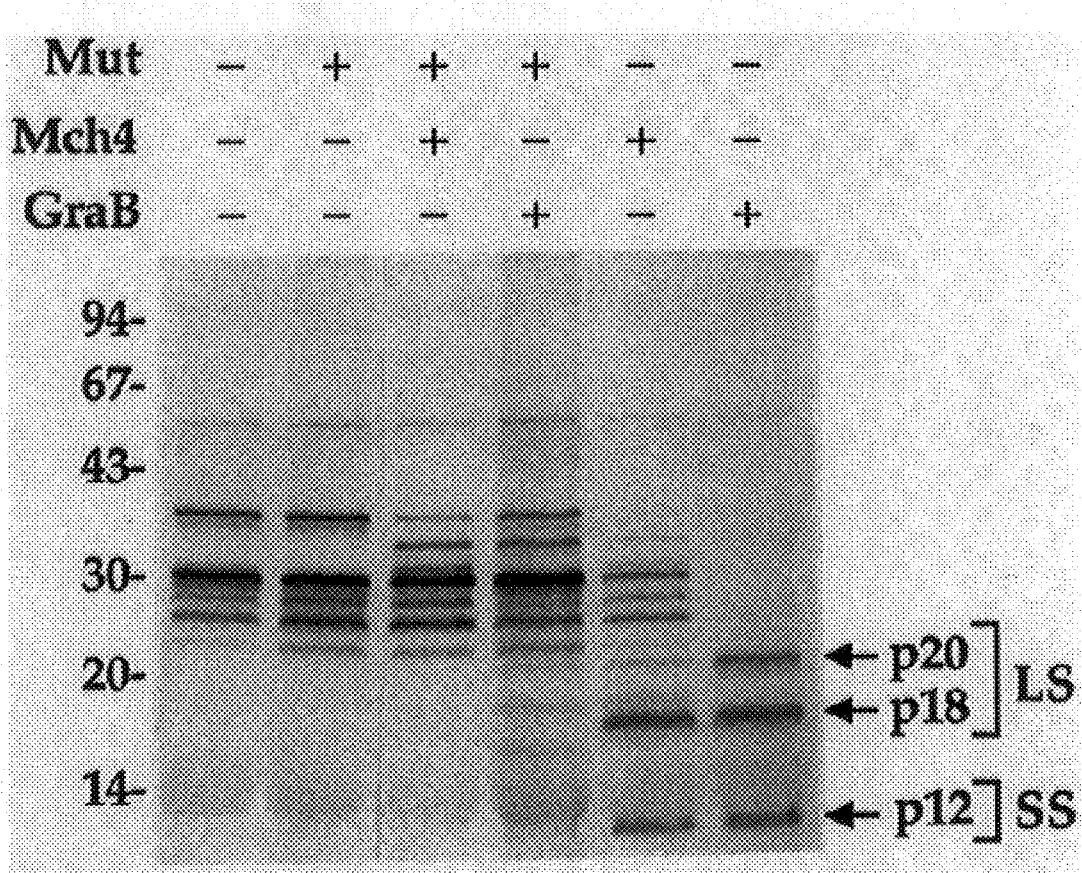
FIG. 5 shows Cleavage of Mch3 and Mch4 proenzymes by Mch4 and granzyme B. (A) Effect of Aspartate mutations on cleavage of proMch3 (A) or Mch4 (B). $^{35}$S-labeled wild type proMch3 (WITH THE lanes), Asp198-mutated proMch3 (M lanes), truncated Mch4-M134 (T1 lanes), truncated Mch4-M235 (T2 lanes) or Asp372-mutated Mch4-M134 (MT lanes) were incubated with recombinant Mch4 (Mch4, +lanes), granzyme B (GraB, +lanes) or buffer (Mch4 and GraB, −lanes) for 1 hour at 37° C. The reaction products were then analyzed by SDS-PAGE and autoradiography. SS, indicates the small subunit. LS, indicates the large subunit.

Like proCPP32, incubation of proMch3 with granzyme B generated the two subunits of the active Mch3 enzyme (FIG. 5A, lane 6). These subunits can be seen as a ~12 kDa band corresponding to the small C-terminal subunit and two ~20 and ~18 kDa bands corresponding to the large N-terminal subunit. The ~20 kDa band is a product of processing at Asp198 between the two subunits, and at Asp23 in the propeptide domain. The ~18 kDa band is a cleavage product of the smaller 30 kDa internally translated product. No cleavage products corresponding to the small or large subunits were observed with the buffer control or the Asp198-mutated proMch3 (FIG. 5A, lanes 1, 2 and 4, respectively).

Unlike CPP32, there was a 33 kDa cleavage product in the Asp198-mutated proMch3 (lane 4). This product is a result of granzyme B cleavage in the propeptide domain of proMch3, indicating that granzyme B can process proMch3 to active Mch3 without the requirement of an additional activity to remove the propeptide domain. Nevertheless, we have shown recently that CPP32 can also cleave the propeptide domain of proMch3 very efficiently (Fernandes-Alnemri et al., supra (1995b)). Consequently, activation of CPP32 in vivo by granzyme B would result in further processing of both CPP32 and its closely related homolog Mch3.

Two truncated Mch4 lacking the N-terminal FADD-like domains were used to analyze cleavage of Mch4 by granzyme B. Mch4-M134 starts with amino acid residue M134 and proMch5-M235 starts with amino acid residue M235. In vitro translation of Mch4-M134 or Asp239-mutated Mch4-M134 (FIG. 5B, lanes 4 and 5, respectfully) generated two major products. These two translation products are observed as a 39 kDa product corresponding to the full length Mch4 and a 27 kDa internal translation product. The internally translated product starts with Met235. This was confirmed by deletion of the cDNA sequence encoding the first 101 amino acids and allowing the translation to proceed from Met102. This deletion produced a truncated Mch4 protein that was similar in size to the internally translated ~27 kDa Mch4 protein (FIG. 5B, lane 1).

Figure 5B:
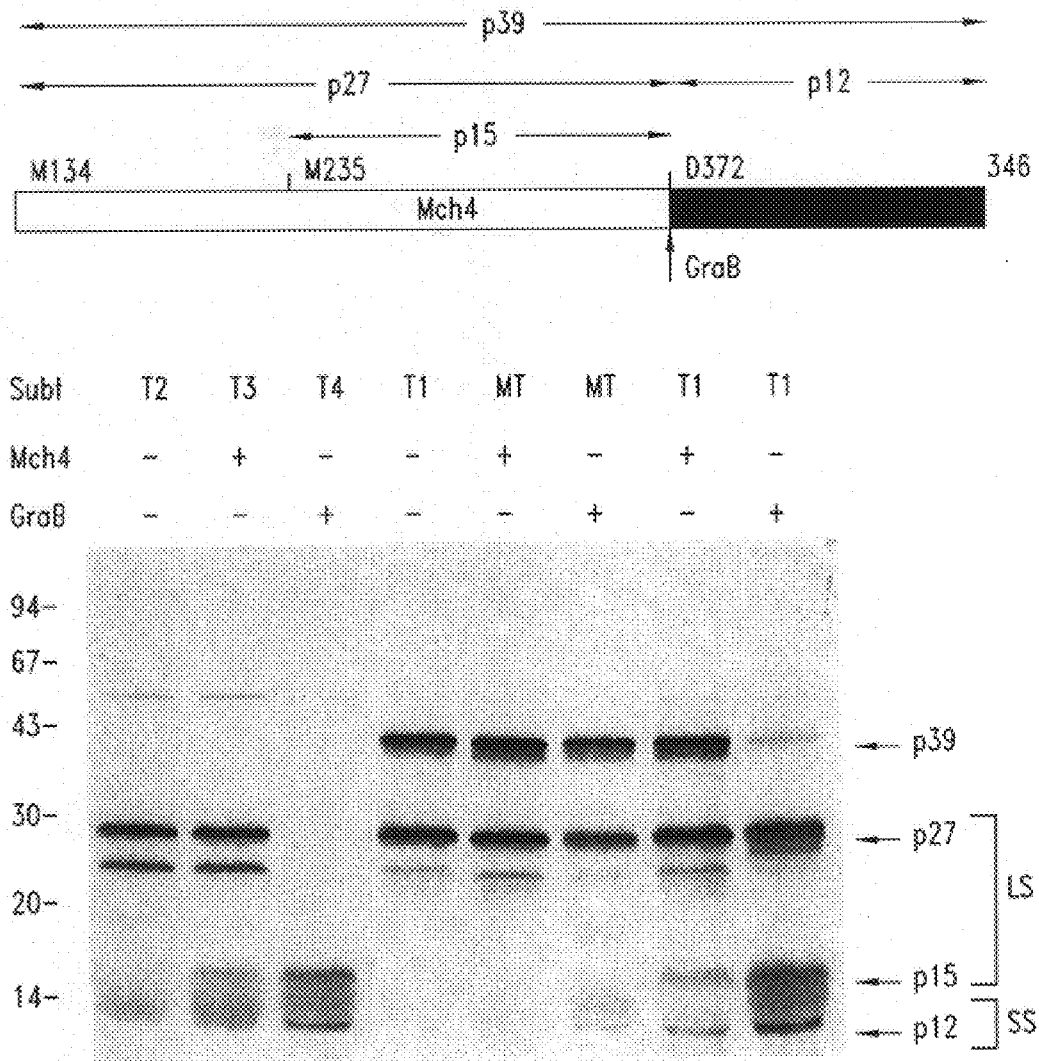

Granzyme B cleaved the truncated Mch4-M235 to generate 15–16 kDa and 12 kDa bands (FIG. 5B, lane 3). On the other hand, Granzyme B cleaved the full length Mch4–M134 to generate ~27 kDa band (large subunit) and 12 kDa band (small subunit) (lane 8). However, because of the presence of the internally translated 27 kDa protein together with the full length Mch4, a 15–16 kDa band was also produced after incubation with granzyme B (lane 8). Like CPP32 and Mch3, the Asp239-mutated Mch4–M134 was not cleaved by granzyme B (lane 6), and there was no cleavage in the buffer control (lanes I and 4).

These data show that granzyme B not only activates pro-CPP32, but also the related ASCPs Mch3 and Mch4 by cleavage at the IETD-S, IQAD-A and IEAD-A putative processing sequences, respectively. Cleavage at these sites generates the two subunits that form the active enzyme complex of these proteases.

EXAMPLE V

Mch4 is Upstream of CPP32 and Mch3 in the ASCP Cascade

This Example shows that Mch4 is capable of activating both proCPP32 and proMch3 while remaining resistant to cleavage from its proenzyme state when incubated in the presence of activated forms of either CPP32 or Mch3.

Evidence suggests that ASCPs are involved in a cascade of activation events which leads to the final cell death signal. To determine whether such a cascade exists within the Ced-3 subfamily of ASCPs occurs, the activation of CPP32 and its closely related homolog Mch3 by another subfamily member such as proMch4 was assessed. Activation was determined by incubating purified recombinant Mch4 with proCPP32 and proMch3.

Figure 6:
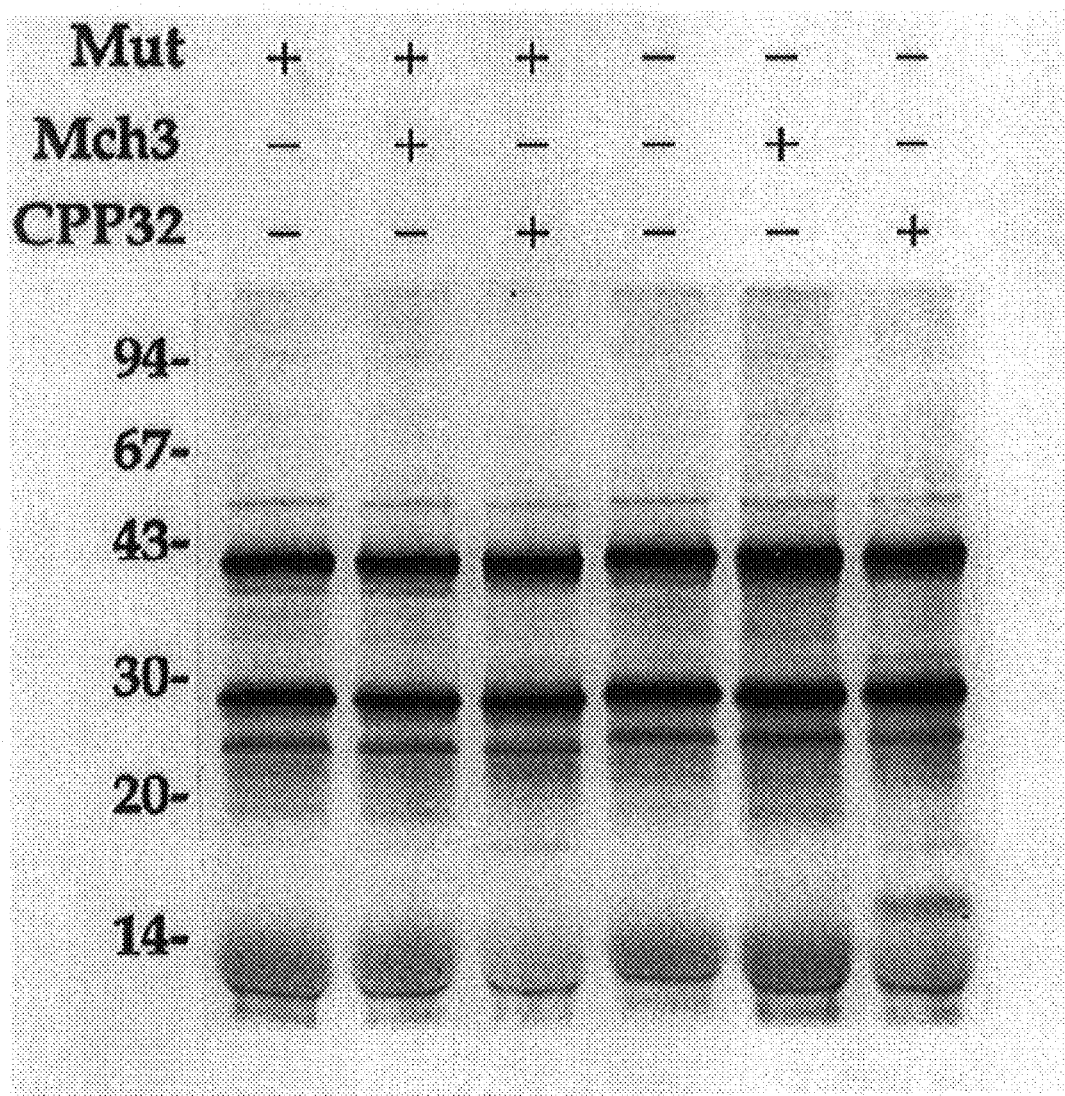
FIG. 6 shows CPP32 and Mch3 activity towards Mch4 proenzyme. 35S-labeled wild type Mch4 (Mut, −lanes) or Asp239-mutated Mch4 (Mut, +lanes) were incubated with recombinant CPP32 (CPP32, +lanes), Mch3 (Mch3, +lanes) or buffer (CPP32 and Mch3, −lanes) for 1 h at 37° C. The reaction products were then analyzed by SDS-PAGE and autoradiography.

Analysis of the cleavage products showed that proMch4 processed proCPP32 and proMch3 and generated cleavage products identical to those produced by granzyme B (FIG. 4A, lane 4 and FIG. 5A, lane 5). Mch4 was unable to process the Asp to Ala mutated proCPP32 and proMch3 (FIG. 4A, lane 3 and FIG. 5A, lane 3). However, like granzyme B, Mch4 was able to cleave the propeptide of Mch3 to generate a 33 kDa band (FIG. 5A, lane 3). Although Mch4 was able to cleave proMch4, its activity towards its proenzyme was significantly lower than that towards proCPP32 and proMch3 (FIG. 5B, lane 7). In addition there was no significant cleavage of proMch4 when incubated with recombinant CPP32 or Mch3 enzymes (FIG. 6). The activity of several other ASCPs such as ICE, TX and Mch2, were also tested but none of these enzymes were able to efficiently process proMch4. These data indicate that Mch4 is upstream of CPP32 and Mch3 in the apoptotic protease cascade.

The above results indicating that proMch4, Mch3 and CPP32 play a role in a protease cascade are further supported by the unique features exhibited by these and related ASCPs. Specifically, ASCPs have two unique features that distinguish them from other proteases. First, they all cleave their substrates after Asp residues, and their activation requires cleavage after Asp residues located in highly conserved processing sites between their large and small subunits. The ability to cleave after Asp residues is only shared with granzyme B, a serine protease that does not however require cleavage after Asp residues for its activation. In addition to these features, both Mch4 and Mch5 contain N-terminal FADD-like death effector domains. The N-terrninal death effector domain of FADD (Hsu et al., *Cell,* 84:299–308 (1996)) can bind one of the two FADD-like domains in either proMch4 or proMch5 for activation and recruitment to FADD-apoptotic pathway. Activation of proMch4 or proMch5 by FADD can, for example, lead to activation of downstream proteases such as CPP32 and Mch3.

The above features indicate that ASCPs interact with and activate each other in a protease cascade fashion as well as acting as substrates for granzyme B. In addition, because multiple ASCP family members coexist in one cell type the ability of one family member to activate several other family members and vice versa results in multiple protease cascades and the generation of multiple apoptotic pathways. Evidence for the existence of multiple apoptotic pathways is corroborated from studies with mice deficient in ICE or Bcl2. For example, thymocytes from ICE deficient mice remain sensitive to glucocorticoid- and ionizing radiation-induced apoptosis, but become resistant to antiFas-induced apoptosis (Kuida et al., *Science* 267:2000–2003 (1995)). On the other hand, T-cells from bc12 deficient mice become more sensitive to glucocortiocoid- and ionizing radiation-induced apoptosis, but less sensitive to antiCD3-induced apoptosis.

Figure 7:
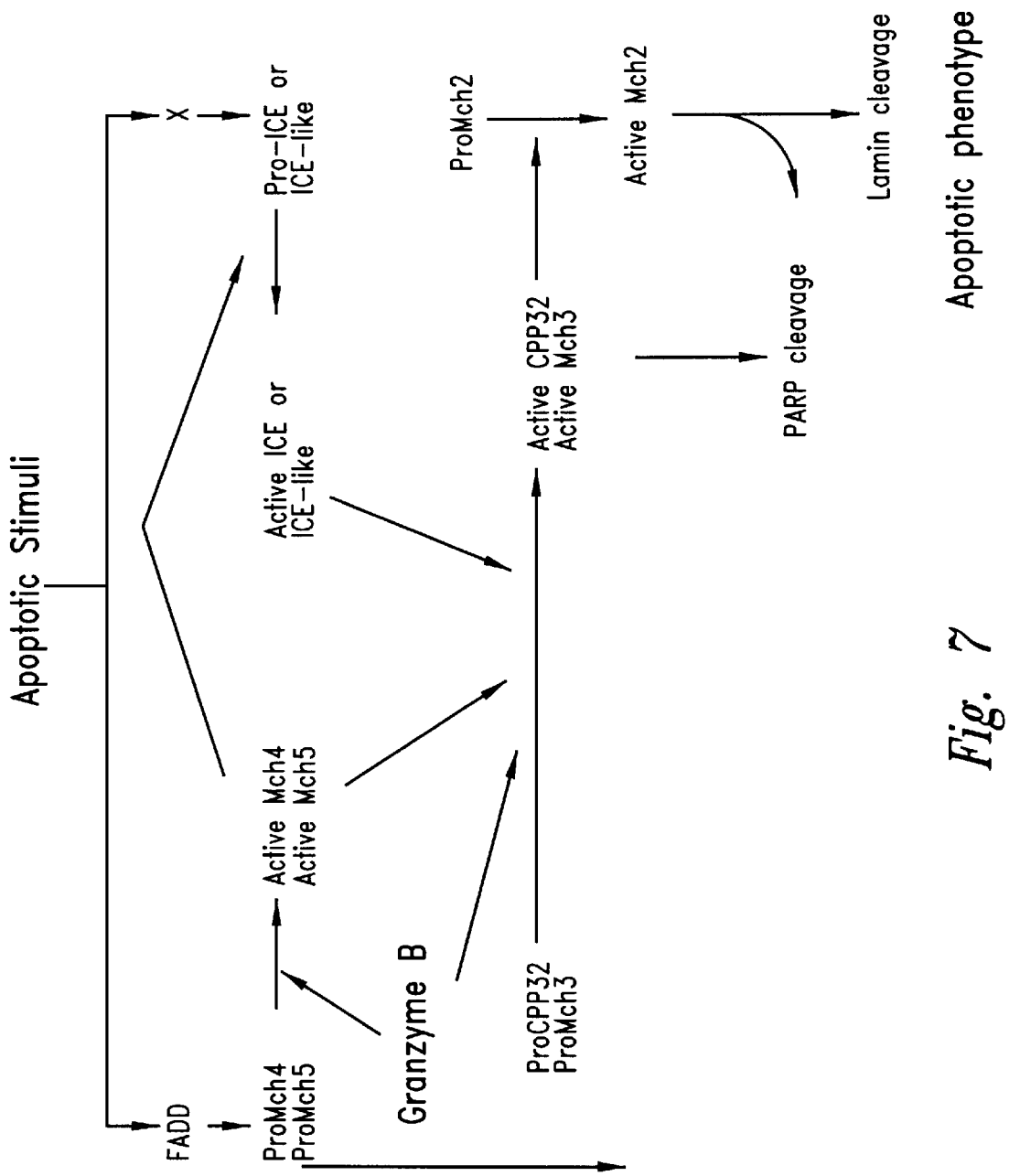
FIG. 7 shows potential apoptotic protease cascades involving the activation of multiple ASCP family members.

As shown in FIG. 7, the above results indicate the existence of multiple protease cascades that can be activated by different apoptotic stimuli. For example, one of these cascades involves proMch4 acting upstream of CPP32, Mch2 and Mch3. Once proMch4 is activated by certain apoptotic stimuli, it can process and activate the proenzymes of Mch3 and CPP32 as shown above. These two ASCPs are likely responsible for PARP cleavage in apoptosis. Active CPP32 can in turn activate proMch2, the only ASCP that can cleave lamin. Because CPP32, Mch3 and proMch4 are poorly inhibited by CnnA (see Table I), the above cascade would not be affected in an ICE-knockout mice, or inhibited by the ICE inhibitor Crm A. Therefore, it is likely that glucocortiocoid- and radiation-induced apoptosis occur through this cascade.

In an alternative ICE or an ICE-like pathway, activation of ICE or an ICE-like ASCP like TX by an apoptotic stimulus or an upstream ASCP results in CPP32, Mch2 and Mch3 activation (FIG. 7). This result is because TX can activate ICE (Faucheu et al., *The EMBO J.* 14:1914–1922 (1995)) and ICE can activate proCPP32 (Tewari et al., *Cell* 81:801–809 (1995)). Furthermore, Mch5 can process proCPP32 and proTX. This ICE-like pathway likely operates in the Fas-apoptotic pathway, since ICE knockout or CrmA abrogate this pathway in some cell types. Also, during Fas-induced apoptosis an ICE-like activity precedes CPP32-like activity (Enari. et al., *Nature* 380:723–726 (1996)). Consequently, FADD likely binds to FADD-like domain in proMch5 or proMch4 for activation and recruitment to Fas-apoptotic pathway. This conclusion is because these domains are capable of both homotypic and heterotypic interactions. Once bound to FADD, proMch5 can undergo autocatalytic processing to the mature enzymes. In this alternative, mature proMch5 could also activate proCPP32 directly, or indirectly by activating proTX. Mature CPP32 would in turn activate the lamin cleaving enzyme Mch2.

The most N-terninal or first domain in both proMch4 and proMch5 (Mch4A; FIG. 3A) are highly related to FADD and likely act as activators of proMch4 and proMch5 by binding the second C-terminal FADD-like (interacting) domain. It is likely that either proMch4 or proMch5 mediates Fas apoptosis by interacting with FADD. However, because they have two N-terminal FADD domains, these polypeptides can be involved in other forms of apoptosis. For example, proMch4 or proMch5 can be repressed under normal conditions by a repressor that sits on its N-terminal FADD domain. Alterations in cellular conditions could release the repressor allowing the N-terminal domain to interact with the second C-terminal FADD-interacting domain leading to activation of proMch4 or proMch5 and consequently activation of downstream proteases such as CPP32, Mch3 and Mch2.

In yet another distinct apoptotic protease cascade an exogenous protease is used to activate multiple endogenous ASCPs. This is the granzyme B-cascade which is used by cytotoxic T-lymphocytes to kill their target cells (see FIG. 7). With the understanding of these multiple cascades and their regulatory activation events, it is now possible to target these pathways either alone or in combination for the therapeutic treatment of human diseases.

EXAMPLE VI proMch4 Exhibits Cell Death Activity

This Example shows the expression of proMch4 and induction of apoptosis in cultured cells.

To determine if proMch4 exhibits cell death activity, the induction of early apoptosis in Sf9 baculovirus cells was assessed. Briefly, Sf9 cells were infected with recombinant baculoviruses encoding full length proMch4 or full length CPP32 as a standard (Femandes-Alnenri et al., *J. Biol. Chem.* 269:30761–30764 (1994)). Cells were then examined microscopically for morphological signs of apoptosis such as blebbing of the cytoplasmic membrane, condensation of nuclear chromatin and release of small apoptotic bodies. In addition the genomic DNA was examined for internucleosomal DNA cleavage.

For the construction of transfer vectors and recombinant baculoviruses, the full length proMch4 in pBluescript KS+ was excised with Bam HI and EcoRI and subcloned into a Bam HI/EcoRI cut pVL1393 vector (Invitrogen, San Diego, Calif.) to generate the pVL-proMch4 transfer vector. The pVL-CPP32 transfer vector was made as described previously (Fernandes-Alnernri et al., supra (1994)). The recombinant transfer vectors were then used to generate recombinant Baculoviruses as previously described (Summers et al., "Manual of Methods for Baculovirus Vectors and Insert Culture Procedures," *Texas Experimental Station Bulletin No.* 1555 (Texas A&M University, College Station, Tex. (1987); and Alnemri et al., J. Biol. Chem. 266:3925–3936 (1991)).

For-the induction of apoptosis in Sf9 cells by proMch4 and CPP32 cells were infected with recombinant baculoviruses AcNPV-proMch4 or AcNPV-CPP32. Apoptosis was measured microscopically by counting cells with the appropriate morphology (blebbing, nuclear condensation).

Alternatively, internucleosomal DNA cleavage is assessed as a characteristic marker. Briefly, total cellular DNA is isolated at 42 h postinfection from either control Sf9 cells or Sf9 cells infected with AcNPV-proMch4 or AcNPV-CPP32 baculoviruses (Alnemri et al. supra (1995)). The DNA samples were analyzed by electrophoresis in a 1.8% agarose gel containing ethidium bromide.

Expression of full length proMch4 in Sf9 cells caused a significant percentage of the cells to undergo apoptosis by about 48 h postinfection which is also manifested by induction of internucleosomal DNA cleavage. These results are consistent with proMch4 being a cell death protease since AcNPV-CPP32 yielded similar results.

EXAMPLE VII

The Mch5 FADD Homology Domain B Induces Apoptosis

To determine if the expression of the FADD-like domain B of proMch5 (Mch5B) can induce apoptosis, it was cloned into a mammalian expression vector and transfected into the MCF7 human breast carcinoma cell line.

Figure 8:
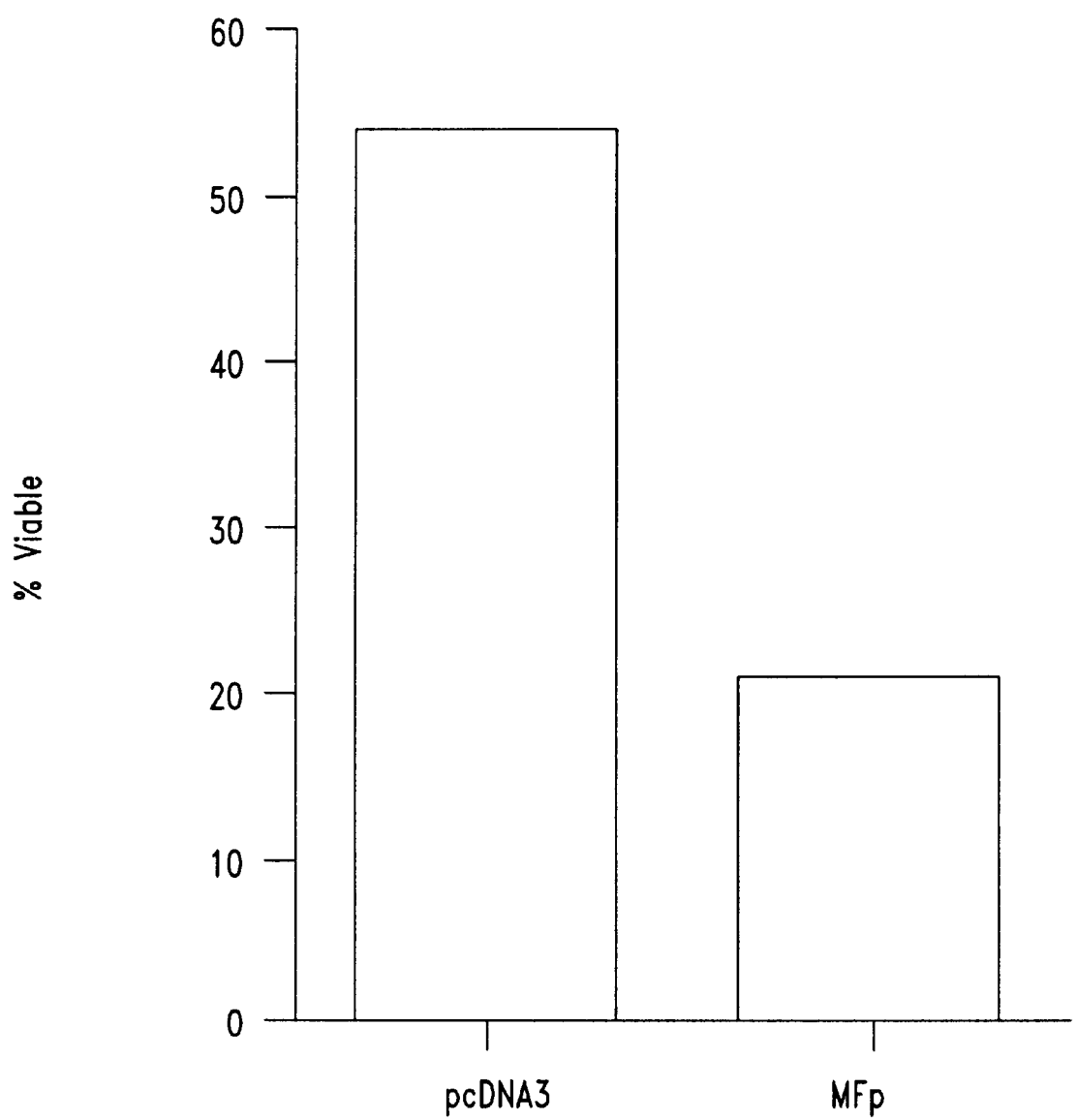
FIG. 8 shows MCF7 cells co-transfected with either plasmid pcDNA3 or Mch5B and pCMV-SPORT-βgal. Following 24 hours post-transfection, cells were fixed and stained with X-gal. Percentage of blue cells that were non-apoptotic is shown (i.e., viable cells). Non-apoptotic cells were distinguished from apoptotic cells by their flattened, spread morphology in the microscope using phase contrast optics (as opposed to rounded, pynotic or apoptotic morphology).

After transfection (36 hours), the percentage of transfected cells that were apoptotic was counted. FIG. 8 shows that in cells transfected with the control plasmid pcDNA3 about 50% of the cells were apoptotic. This result is likely due to the induction of apoptosis by the lipofection reagent used for DNA transfection. In contrast, about 80% of the cells transfected with Mch5B were apoptotic (FIG. 8). Thus, heterologous expression of Mch5 FADD-like domain B induces apoptosis in these cells.

The induction of apoptosis by Mch5B indicates that the mechanism by which Mch5B induces apoptosis is similar to the way in which the homologous domain in FADD (the FADD death effector domain) induces apoptosis when expressed by transfection. This mechanism involves binding of the Mch5 FADD-like domain to either the proMch4 or proMch5 pro-domains, binding induces activation of the proMch4 or proMch5 proteases and induction of apoptosis.

Briefly, Mch5B was subcloned into the mammalian expression vector pcDNA3. The Mch5 cDNA in the vector pBluescript KS was used as a template for PCR amplification of the Mch5 FADD B domain using the following primers: 5' primer: CCTACAGGATCCACTTCTGCCG-CATGAGC; 3' primer: ACTCCTCCCCTTTGCTGAAT-TCTTAATAGTCGT. The PCR product was cut with BamHI and EcoRI and ligated into BamHI/EcoRI cut pcDNA3 to produce the Mch5/Fadd B/pcDNA3 (MFp) vector. MFp DNA was transduced into DH5α bacteria and DNA was purified. For transfection, MFp or pcDNA3 (1.8 μg) were mixed with the liofectin reagent (GIBCO Life Technology) and 0.2 μg of plasmid pCMC-SPORT-βgal (GIBCOBRL Catalogue #10586–014) and applied to 50% confluent cultures of MCF7 cells for eight hours at 37° C. The cells were then washed and growth media added. After 36 hours cells were fixed in 10% para-formaldehyde and β galactocidase expression visualized by incubating cells with X-gal substrate solution.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method for identifying a compound that modulates Mch4 or Mch5 activity, comprising:
   (a) contacting a sample containing Mch4 or Mch5, or a functional fragment thereof with a test compound; and
   (b) detecting the activity of Mch4 or Mch5, or a functional fragment thereof, wherein a change in activity indicates a compound which modulates Mch4 or Mch5 activity.

2. The method of claim 1, wherein said modulation comprises inhibition of Mch4 or Mch5 activity.

3. The method of claim 1, wherein said activity is detected by a binding assay.

4. The method of claim 1, wherein said activity is detected by turnover of a substrate.

5. The method of claim 4, wherein said substrate comprises a site cleaved by Mch4 or Mch5 selected from the group consisting of a protein, a polypeptide, and a peptide.

6. The method of claim 5, wherein the substrate comprises a peptide selected from the group consisting of DEVD and YVAD.

7. The method of claim 5, wherein said substrate is a fluorogenic substrate.

8. The method of claim 7, wherein said fluorogenic substrate is selected from the group consisting of DEVD-AMC and YVAD-AMC.

9. The method of claim 1, wherein said sample comprises a cell lysate.

10. The method of claim 1, wherein said sample comprises substantially pure Mch4 or Mch5 or a functional fragment thereof.

* * * * *